United States Patent [19]
Meador et al.

[11] Patent Number: 5,785,044
[45] Date of Patent: Jul. 28, 1998

[54] FLUID SAMPLE RECEPTACLE

[75] Inventors: James W. Meador; Thomas L. Kraft, both of Houston, Tex.; David O'Bryan, Kennett Square, Pa.; John F. Berry; Thomas G. Miller, both of Houston, Tex.; Norman Hugh Smith, Bothell, Wash.; William S. Schnorr, Pittsburgh, Pa.; Christopher T. Nikirk, Houston, Tex.; Louis A. Waters, Jr., Bellaire, Tex.; Sean M. Donnelly, Houston, Tex.

[73] Assignee: KVM Technologies, Inc., Houston, Tex.

[21] Appl. No.: 634,521

[22] Filed: Apr. 18, 1996

Related U.S. Application Data

[63] Continuation of Ser. No. 180,872, Jan. 11, 1994, abandoned, which is a continuation-in-part of Ser. No. 27,860, Mar. 8, 1993, abandoned.

[51] Int. Cl.$^6$ .................................................. A61B 19/00
[52] U.S. Cl. .............................. 128/760; 206/221; 422/61
[58] Field of Search ........................ 128/760; 206/221, 206/438, 569; 422/61

[56] References Cited

U.S. PATENT DOCUMENTS

| | | | |
|---|---|---|---|
| 2,689,566 | 9/1954 | Lockhart | 206/221 |
| 2,793,776 | 5/1957 | Lipari | 206/221 |
| 4,221,295 | 9/1980 | Tuchband | 206/569 |
| 4,315,570 | 2/1982 | Silver | 206/221 |
| 4,408,905 | 10/1983 | Ehrenkranz . | |
| 4,458,811 | 7/1984 | Wilkinson | 206/219 |
| 4,512,471 | 4/1985 | Kaster | 206/438 |
| 4,599,219 | 7/1986 | Cooper | 422/61 |
| 4,761,379 | 8/1988 | Williams et al. | 435/296 |
| 4,769,215 | 9/1988 | Ehrenkranz . | |
| 4,852,560 | 8/1989 | Hermann, Jr. et al. . | |
| 4,936,446 | 6/1990 | Lataix | 206/221 |
| 4,961,432 | 10/1990 | Guirguis | 128/760 |
| 4,986,322 | 1/1991 | Chibret et al. | 141/319 |
| 5,084,041 | 1/1992 | Oxley et al. | 604/410 |
| 5,088,627 | 2/1992 | Musel | 222/145 |
| 5,160,329 | 11/1992 | Oxley | 604/317 |
| 5,186,900 | 2/1993 | Jensen et al. | 422/104 |
| 5,217,443 | 6/1993 | Oxley | 604/317 |
| 5,353,961 | 10/1994 | Debush | 206/221 |
| 5,380,289 | 1/1995 | Hemstreet | 128/760 |
| 5,423,792 | 6/1995 | Oxley . | |
| 5,599,331 | 2/1997 | Hemstreet et al. | 128/760 |

*Primary Examiner*—Terrance Till
*Attorney, Agent, or Firm*—Tim L. Burgess

[57] ABSTRACT

A fluid sample receptacle provides a means of assuring uncontaminated, multiple samples of a fluid specimen. An upper or isolated sample chamber and a lower or primary sample chamber provide redundant test samples. A cover or lid with a downwardly extending column includes a stopper with a removable plug attached to automatically seal the lower sample chamber when the cover is sealed across the top of the upper chamber. This feature guarantees that the sample chambers are sealed or isolated simultaneously and that the test samples are therefore identical when taken. Tamper evident seals prove that either sample has not been contaminated. A preferred embodiment provides a bellows assembly to accommodate variations in ambient pressure and to provide a positive means of expelling a precise quantity of fluid from the receptacle for testing.

41 Claims, 16 Drawing Sheets

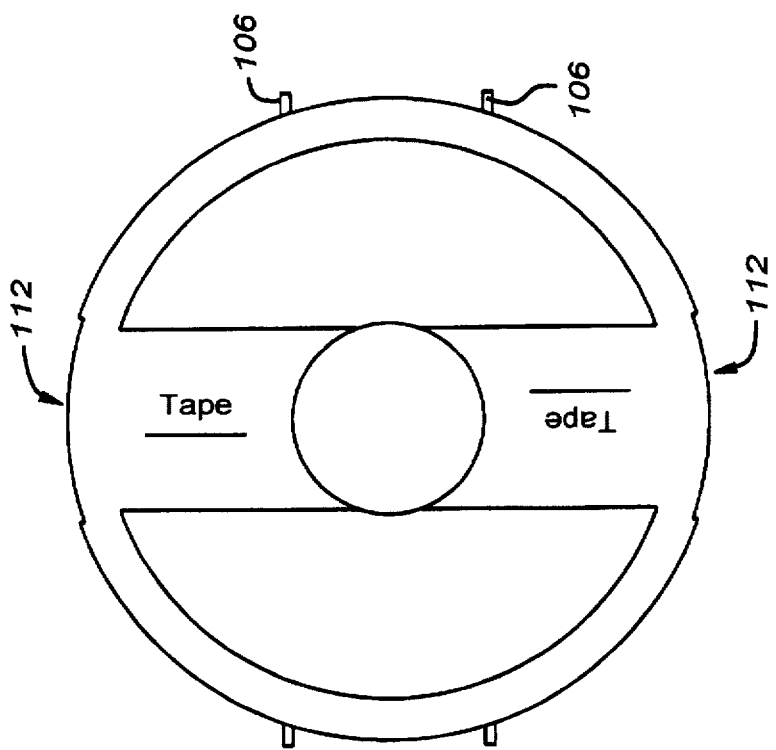
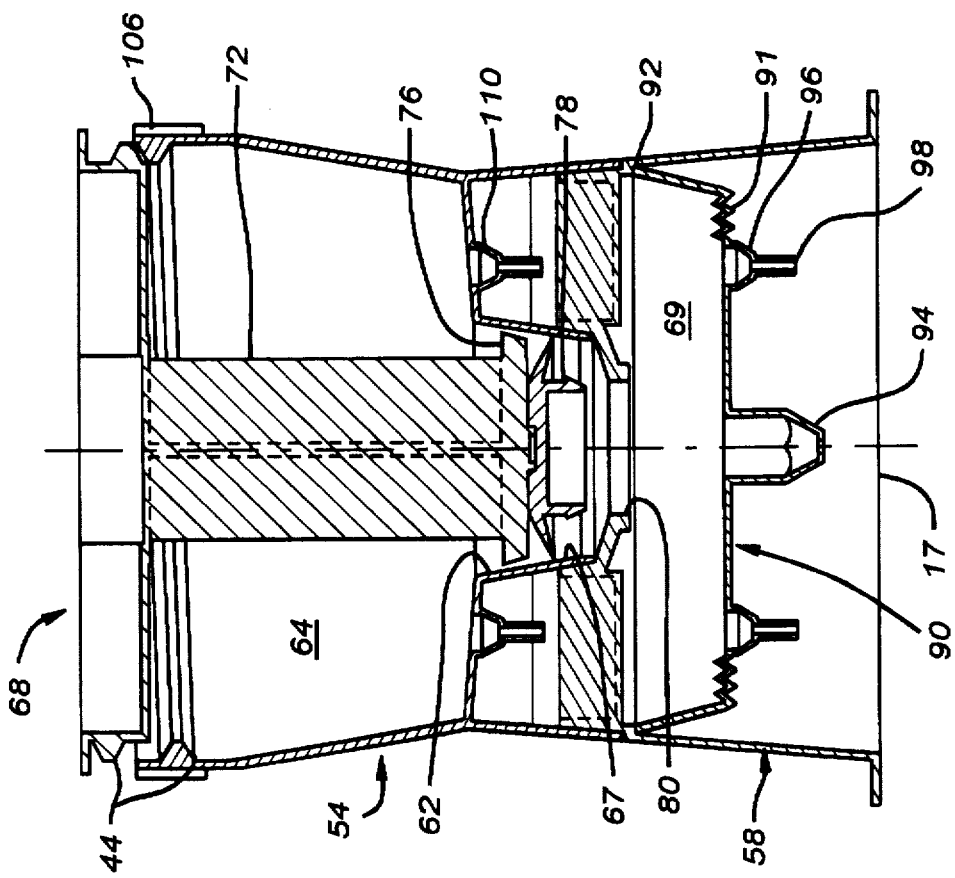
FIG. 4B
FIG. 4A

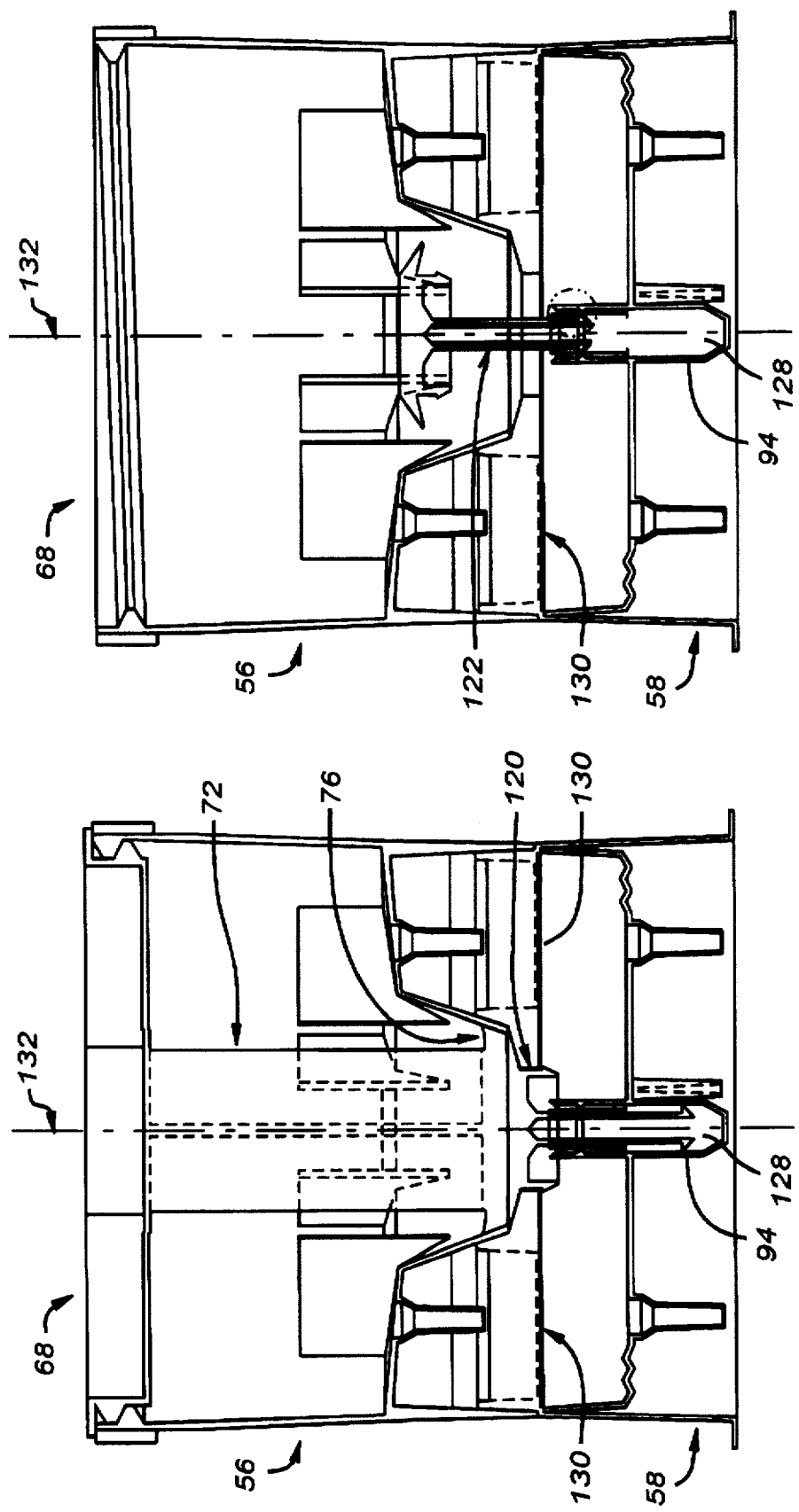

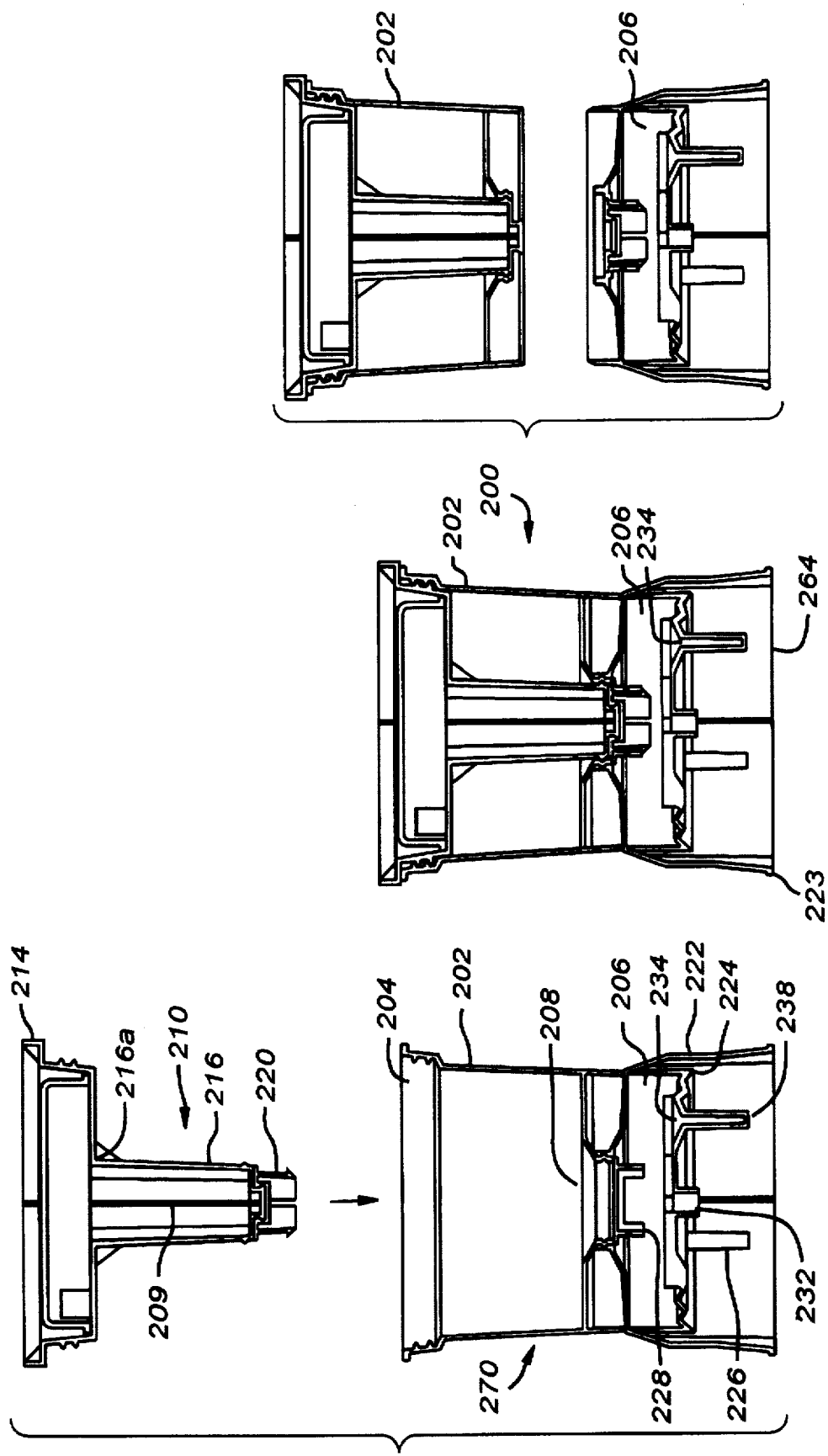

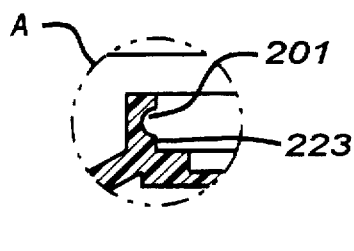
FIG. 9Fi
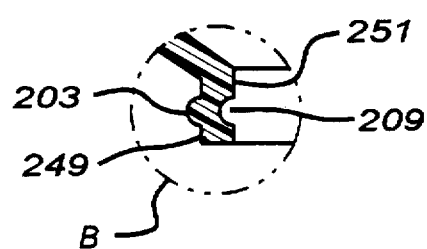
FIG. 9Fii
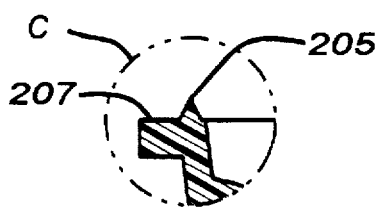
FIG. 9Fiii
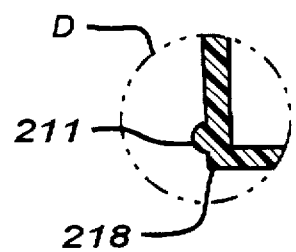
FIG. 9Fiv
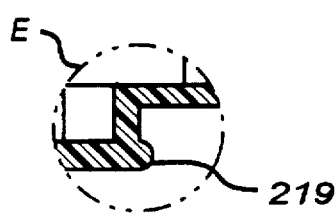
FIG. 9Fv
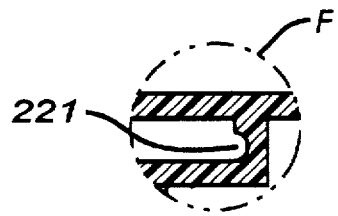
FIG. 9Fvi
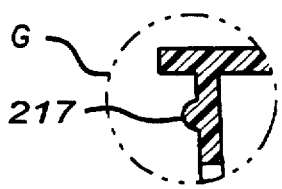
FIG. 9Fvii
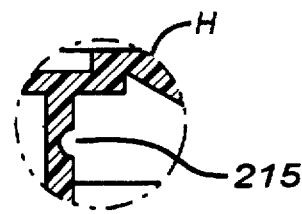
FIG. 9Fviii

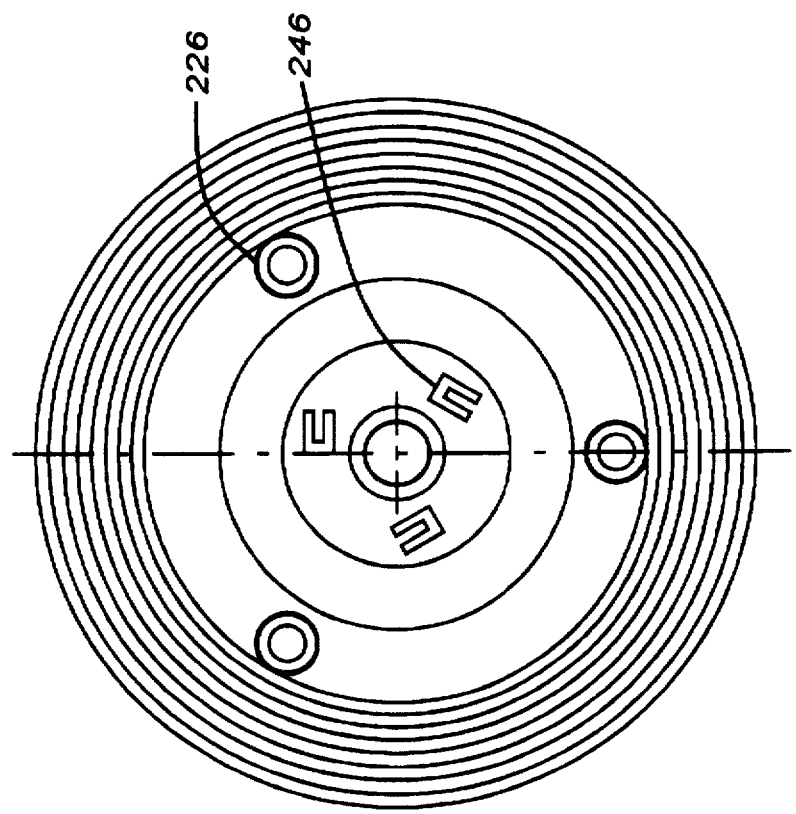
FIG. 10B
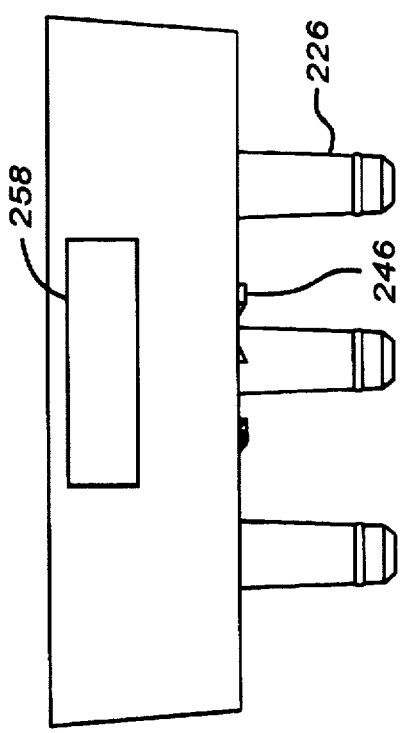
FIG. 10A
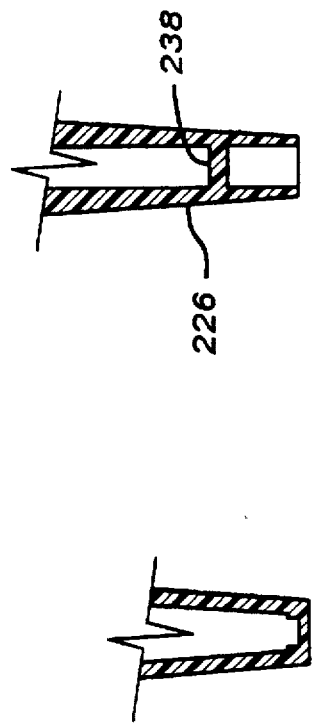
FIG. 10H
FIG. 10G

FLUID SAMPLE RECEPTACLE

This application is a continuation of U.S. application Ser. No. 08/180,872, filed Jan. 11, 1994, now abandoned, which is a continuation-in-part of U.S. application Ser. No. 08/027,860, filed May 8, 1993, now abandoned.

FIELD OF THE INVENTION

The present invention relates generally to the field of fluid sampling and testing and more particularly to a tamper-evident urine sample receptacle that provides for redundant isolated samples.

BACKGROUND OF THE INVENTION

In fields such as clinical medicine, forensic sciences, environmental quality testing, food quality assurance, drug testing, and other areas, it has become possible to determine the presence and/or amount of trace substances in test samples even when such substances are present in very low concentrations (on the order of parts per million, or even billion). For example, during testing of urine, it is now possible to detect and quantify trace quantities of most known illicit drugs. Further, as a result of such drug testing, positive test results may have a profound impact on the donor's career or employment. In the proper circumstances, positive test results may also result in criminal liability for the donor.

Such circumstances dictate that the security or chain-of-custody of the sample be preserved and that any tampering of the sample be immediately apparent. It is also desirable that test results be verified by repeating the tests on an identical sample. It is also important that sample be capable of being "split", or a secure portion of the sample be sent to another laboratory for confirmation of the test results.

Similarly, other fluid sampling procedures present the same issues of repeatability and integrity verifiability. For example, the U.S. Environmental Protection Agency conducts a variety of ongoing testing programs. These testing programs are intended to guarantee compliance with standards for maximum levels of toxic and/or radioactively contaminated fluids, such as plant effluent. In the event of a test indicating non-compliance with such a standard, it is important that the EPA be able to repeat the test on another, identical sample. It is equally important that the EPA be able to verify that the sample that is tested is indeed the sample that was taken and that no foreign substances have been introduced into the sample without being tamper evident.

Thus, there remains a need for a fluid sample receptacle that provides for more than one isolated specimen of a sample. Such a receptacle should provide for splitting of the sample. The receptacle should be easy to use and simple in construction. It should also minimize or even eliminate the possibility of contamination of the test sample. Further, the receptacle should automatically retain an archival sample specimen so that any tests may be repeated on an identical test sample and the results of the tests verified.

Such a sample receptacle should also present a geometric aspect that is sufficiently simple to be easily moldable by known molding techniques.

SUMMARY OF THE INVENTION

The present invention provides these and other features of a test sample receptacle. An upper or isolated sample chamber accessed by an opening is connected by a flow passage to a lower or primary sample chamber. The upper and lower chambers are separable from each other to provide redundant sample chambers. Means are provided to seal (1) the access opening of the upper chamber, (2) the portion of the connecting passage from the upper chamber, and (3) the portion of the connecting passage into the lower chamber, so that the upper and lower chambers remain sealed when the two chambers are separated. An upper chamber cover or lid with a downwardly extending column includes an upper plug portion and a separately attached lower plug portion to seal the passage into the lower chamber when the lid closes and seals the upper chamber access opening and the upper portion of the connecting passage. This feature guarantees that the sample chambers are sealed and isolated simultaneously and that the test samples are therefore identical. Means are provided to access the isolated samples in the upper and lower chambers without breaking the three seals. Tamper evident guards can be employed with the lid and plug seals to prove that neither sample in either chamber has been adulterated by access through one of the three seals. Means also are provided to prevent disruption of the seals as a result of pressure changes experienced by the receptacle between the time of sample collection and receptacle sealing and the times when the samples in the isolated chambers are accessed and tested. The configuration of the receptacle providing these mechanisms is advantageous in that it lends itself to being easily moldable.

These and other objects and features of the present invention will be apparent to those of skill in the art when they read the following detailed description in conjunction with the drawing figures.

BRIEF DESCRIPTION OF THE DRAWINGS

FIG. 4A is a side sectional view of another embodiment of the present invention.

FIG. 4B depicts a top view of the closure lid in FIG. 4A for sealing the receptacle of FIG. 4A.

FIGS. 6A–6D depict an embodiment of the receptacle of this invention in which a plug element is included as part of a lower sample chamber, rather than as a part of a closure lid as in other embodiments. FIG. 6A is a side elevational view of the receptacle lid stem. FIG. 6B is a top view of the receptacle without the lid stem. FIG. 6C is a partial side sectional view of the assembled receptacle with the lid stem in sealing position. FIG. 6D is a side sectional view of the receptacle seen from the top in FIG. 6C, showing the plug element in a pre-use elevated position.

FIG. 9b is an exploded side sectional view of a partially assembled specimen collection container of FIG. 9a.

FIG. 9c is a side sectional view of a partially assembled specimen collection container of FIG. 9a.

FIG. 9d is a side sectional view of an assembled specimen collection container of FIG. 9a.

FIG. 9e is a side sectinal view of a specimen collection container of FIG. 9a separated into two container portions.

FIGS. 9Fi–9Fviii are a collection of enlargements or "zoom" details of the portions of the structure encircled and labeled A–H in FIG. 9B.

FIG. 10a is side elevational view of a modified primary collection chamber bellows assembly of the specimen collection container of FIG. 9.

FIG. 10b is a bottom plan view of the modified primary collection chamber bellows assembly of FIG. 10a.

FIG. 10c is a side sectional view of the modified primary collection chamber bellows assembly of FIG. 10a.

FIG. 10d is a bottom perspective view of the modified primary collection chamber bellows assembly device of FIG. 10a.

FIG. 10e is a top perspective view of the modified primary collection chamber bellows assembly device of FIG. 10a.

FIG. 10g is a side cross sectional view of a nozzle portion suitably in the container of FIGS. 9a–e and 10a–f.

FIG. 11b is a side sectional view of the device of FIG. 11a.

DETAILED DESCRIPTION OF PREFERRED EMBODIMENTS

Figure 1A:
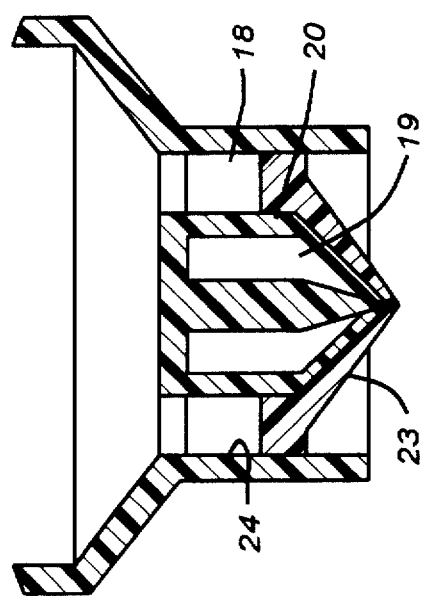
FIG. 1A provides a side sectional detail of an embodiment of a cap sleeve comprised in the present invention.
Figure 1:
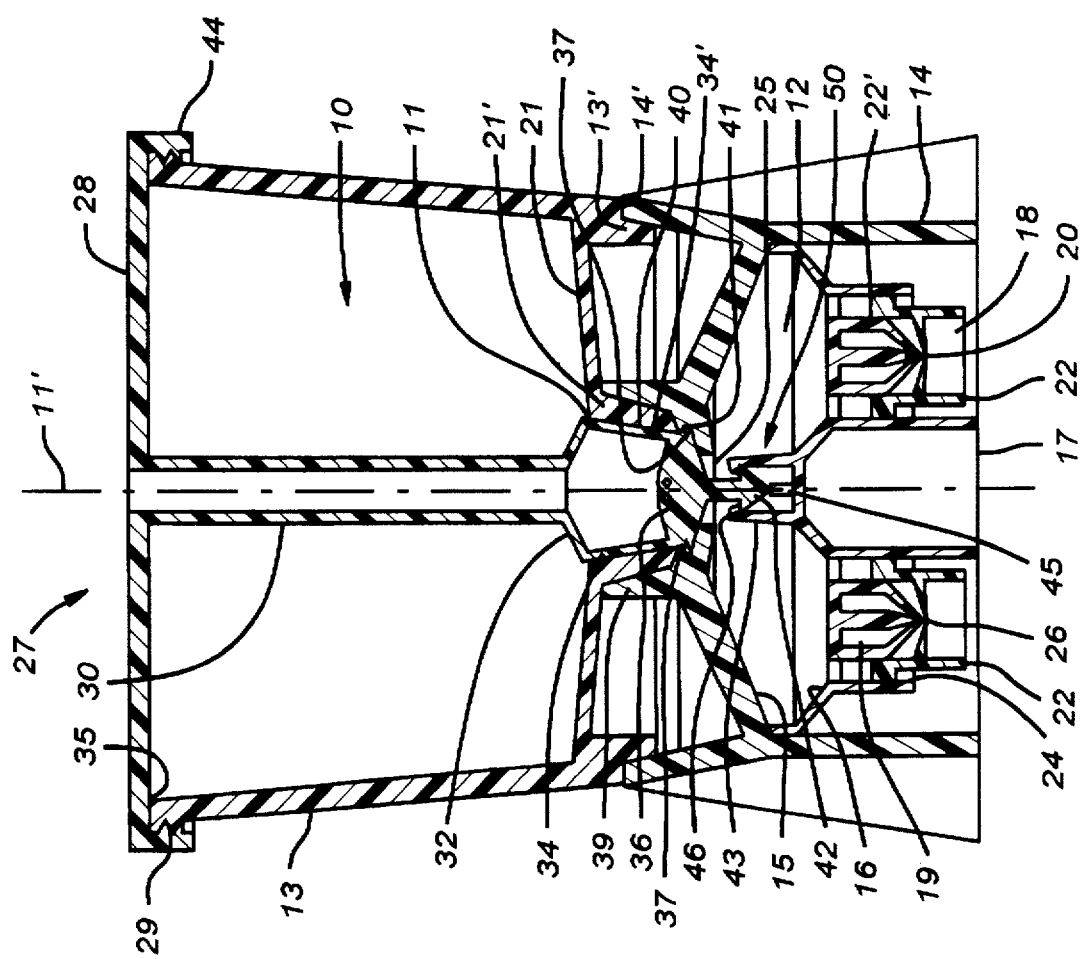
FIG. 1 is a side sectional view of an embodiment of a specimen receptacle of the present invention.

Referring to FIG. 1, a specimen receptacle of the present invention comprises an upper sample chamber 10 and a lower sample chamber 12, in fluid communication with upper chamber 10 through a flow passage 11 more particularly described below. Through flow passage 11 fluid from upper chamber 10 can enter lower chamber 12. Upper sample chamber 10 also may be referred to as an isolatable sample chamber, and the lower chamber 12, as a primary sample chamber. Upper sample chamber 10 suitably is molded in one piece and includes a generally circular wall 13, tapered radially inwardly and downwardly to a shouldered annular flange 13' at the base of wall 13. Connected to the interior circumference of wall 13 above shouldered annular flange 13' is upper chamber floor 21. Floor 21 is radially inwardly declined to a central inlet to passage 11. An upper portion of passage 11 is formed by the interior surface of a wall of an inwardly tapering tubular portion 21' extending down from floor 21.

The lower (primary) sample chamber 12 comprises a circular base wall 14, a roof 15 and a lower chamber floor 16.

Upper sample chamber 10 is geometrically coaxially aligned and snugly fitted to lower sample chamber 12, along an axis 11' centered in flow passage 11. This is accomplished by location of shouldered annular flange 13' slightly interferingly coaxially inwardly of a circular base wall 14 of the primary sample chamber 12, with the shoulder of flange 13' resting on a rim 14' of base wall 14.

The base wall 14 and the floor 16 of lower sample chamber 12 are sealed together, suitably by friction-heat welding (by, for example, spinning the base wall 14 and well floor 16 relative to one another), or by solvent or ultrasonic welding, or by other appropriate means.

Roof 15 of lower chamber 12 inclines radially inwardly to an outlet 25 to passage 11 formed centrally about axis 11'. The topside of roof 15 includes an upstanding bowl portion 39. The bottom of bowl 39 recesses into a basin 40 containing a central basal opening 40'. Central basal opening 40 forms the lower portion of passage 11. The walls of bowl 39 are shaped interiorly to interferingly fittingly nest therein the outer surface of tubular portion 21'. The top of the bowl wall supports a central portion of upper chamber floor 21. The walls 41 of basin 40 are interiorly threaded.

Lower sample chamber floor 16 includes a plurality of sample acquisition access ports 18. A preferred embodiment includes four such access ports 18, although only one access port is required. The access ports 18 provide an important feature of the present invention, ensuring "tamper-proof" integrity of a fluid sample contained in lower sample chamber 12.

The access ports 18 include apertures 19 to chamber 12 and an aperture closure 22. The access port embodiment depicted in FIG. 1 includes at least one flow guide 20 that defines the size of the apertures 19, and the aperture closure 22 of each access port 18 takes the form of a penetrable cap sleeve. Preferably, the cap sleeve 22 slides snugly within the inside surface of the access port walls 24 and against the outside surface of the flow guide 20. In this way, a flange 22' on the cap sleeve 22 is slightly compressed between the access port walls 24 and the flow guide 20 to improve the sealing ability of the cap sleeve. The penetrable cap sleeve 22 includes a penetrable membrane 26. The base wall 14 is footed and enclosed with a tamper evident seal 17.

FIG. 1A depicts another combination of an access port/ cap combination. This embodiment involves mechanically sealing and unsealing of a sample port. In this approach, the lower portion of the flow guide 20 is conical and also has a plurality of apertures 19 in the conical portion. This conical portion of the flow guide 20 may be referred to as the flow port. A conically shaped cap sleeve 23 fits the flow guide 20 to close off the apertures 19 formed in the conical lower end of the flow guide. The flow guide may take other shapes so long as the sleeve 23 conforms to the shape of the lower end of the flow guide. With the conical sleeve 23 impressed against the conical flow port, no flow occurs.

Lower floor 16 also includes a centally located keeper 50 coaxially aligned with opening 11. Keeper 50 comprises an upright tubular portion 43 terminating in a plurality of spaced radially inwardly projecting detent ended fingers 46, the detents having a declined upper surface facing toward the axis 11' and a lower surface aligned substantially normal to the inner wall of tubular portion 43. A stop 45 is coaxially centered within the walls of tubular portion 43 and projects upwardly from well floor 16 terminating short of the detents of fingers 46.

The receptacle of the present invention also includes a receptacle closure indicated generally by reference numeral 27. Closure 27 includes a top or lid 28, formed with an outer annular flange 44, the inner flange surface of which is shaped into threads cooperatively engageable with companion external threads provided on the outer upper wall portion 29 of upper chamber 10. Joined to the under side of lid 28 is a vertical stem or column portion 30 co-axial with flow passage 11 interconnecting the upper and lower sample chambers 10 and 12. The lower end of the vertical stem 30 is connected by an annular flexure 32 to an inverted hollow frustoconical upper plug portion 34. The frustoconical upper plug portion 34 is matingly receivable in companionally inwardly tapered walls of tubular portion 21'. The bottom of upper plug 34 is separably connected to a lower screw plug portion 36 by a deformable to failure breakpiece, shear pin or other suitable means 34'. The outer wall 37 of lower screw plug portion 36 is exteriorly threaded. Extending downwardly from plug 36 by an arm and centered in axis 11' is a conical stabber portion 42.

The foregoing structure cooperates as follows. At the collection point, when a specimen is to be taken, the sample cup or receptacle is completely assembled except for the receptacle top 28. The donor introduces fluid into the upper chamber 10 through the top opening 35 thereto, and the fluid flows into the lower chamber 12 through passage 11. The upper specimen chamber 10 fills after the lower chamber 12 fills. Upper specimen chamber 10 and lower specimen chamber 12 are then closed and sealed apart, using the closure assembly 27. Receptacle top 28 is centered above the mouth of the receptacle and stabber 42 of stem 30 is placed through passage 11 and positioned aligned between the detent ends of fingers 46 of keeper 50. This matingly introduces frustoconical portion 34 into passage 11 and juxtaposes lower screw plug 36 and external screw threads 37 in basin 40 at internal threads 41. The wall 37 of screw plug 36 is then threadingly engaged, top 28 is rotated, and lower screw plug 36 is screwed into the companionally threaded walls 41 of basin 40 in bowl portion 39 of roof 15 of the lower collection chamber 12. As plug 36 is screwed in, the frustoconical portion 34 connected to the stem 30 of closure 28 advances to a seating and sealing position in passage 11 interconnecting upper chamber 10 and lower chamber 12. As the frustoconical portion 34 advances and plug 36 screws into place, conical stabber 42 is forced down the inclined upper surface of detent finger ends 46, spreading the fingers radially outwardly until the conical base of stabber 42 advances past the barb ends, allowing the fingers to return to their unspread home position and capture stabber 42 within keeper 50. This irreversably locks lower plug 34 into a screwed-in sealing position. Stop 45 prevents further advance of stabber 42 in keeper 50 and disallows continued screwing advance of plug 36 in basin 40, maintaining the seal at outlet 25 of passage 11. At the point where stop 45 prevents further advance of lower screw plug 36, frustoconical upper plug 34 is seated axially in the upper portion of passage 11. Once frustoconical plug 34 seats, resistance is met, and top 28 is pushed down to engage the threads on flange 44' of receptacle closure top 28 and the companionally threaded upper outer portion 29 of wall 13 of the isolated sample container. By pushing down the top, the bottom of stem 30 and frustoconical portion 34 is pushed toward screw plug 36. This evacuates any volume of the fluid sample remaining in passage 11 so that no sample drips or is left if and when the isolated sample container is later separated from the primary sample container. As the top is pushed down further, the stem pushes the top walls of the hollow upper plug 34 toward a horizontal position which seats the plug against the walls of passage 11 in the isolated sample container. That is to say, the lateral juncture of flexure 32 and frustoconical upper plug 34 is fixed from further axial movement, and the axial push of stem 30 vertically depresses the central joinder of flexure 32 and stem 30, collapsing the flexure toward plug 36. This press fits frustoconical upper plug portion 34 in passage 11 and seals the inlet of passage 11. Top 28 is then rotated on the threads and screwed down. Screwing top 28 onto the isolated sample container deforms to the point of failure the material that connects the bottom of upper plug 34 plug to the lower screw plug 36. Once this connection fails the samples are totally isolated.

In use, when the sample within the lower sample chamber 12 is to be accessed for testing, the tamper evident foot seal 17 is removed. Next, cap sleeve 22 is slidingly displaced upwardly against the pointed end of flow guide 20, which punctures or penetrates the membrane 26. A sample of the specimen in lower chamber 12 then flows out through the apertures 19 in flow guide 20 for capture and testing. The rate of flow of sample from chamber 12 is influenced by the size of the apertures 19. The upward displacement of cap sleeve 22 suitably is accomplished by a testing instrument which manually or mechanically slides the cap sleeve 22 upwardly against the pointed end of flow guide 19 and receives the released sample.

Alternatively, in the form of the sleeve conforming cap 23, shown in FIG. 1A, the testing instrument axially removes the conical sleeve 23 from conforming contact with the flow port, allowing fluid to flow from the sample container. Replacing the sleeve 23 against the conical flow port mechanically seals the system and prevents reuse of that particular access port (although other access ports may still be used to take backup verification sample portions).

The shape and fit of the receptacle and the mentioned optional or alternative retaining ridges keep the upper and lower sample chambers connected. With the upper and lower chambers sealed as has been described, when a confirmation sample of the specimen in the upper and lower chambers of the receptacle is desired, the upper chamber can be separated from the lower chamber by a slight torqing motion applied to the upper chamber while the lower chamber is fixed from movement. Then, the isolated sample in the upper chamber 10 can be sent to an independent lab. The primary sample chamber remains sealed in the lower chamber because lower plug 36 remains with the lower sample chamber while the frustoconical portion or upper plug 34 remains with the upper sample chamber.

Figure 3:
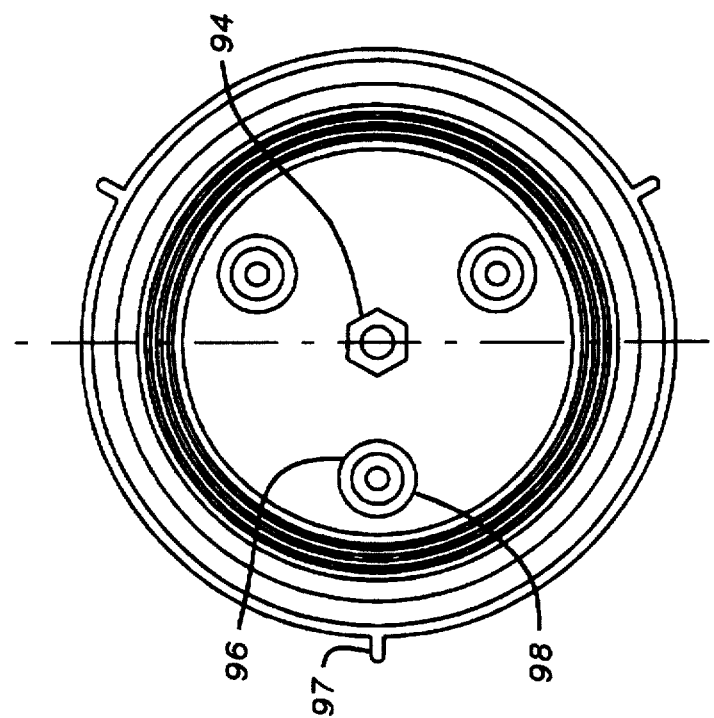
FIG. 3 is a bottom view of the embodiment depicted in FIG. 4.
Figure 2:
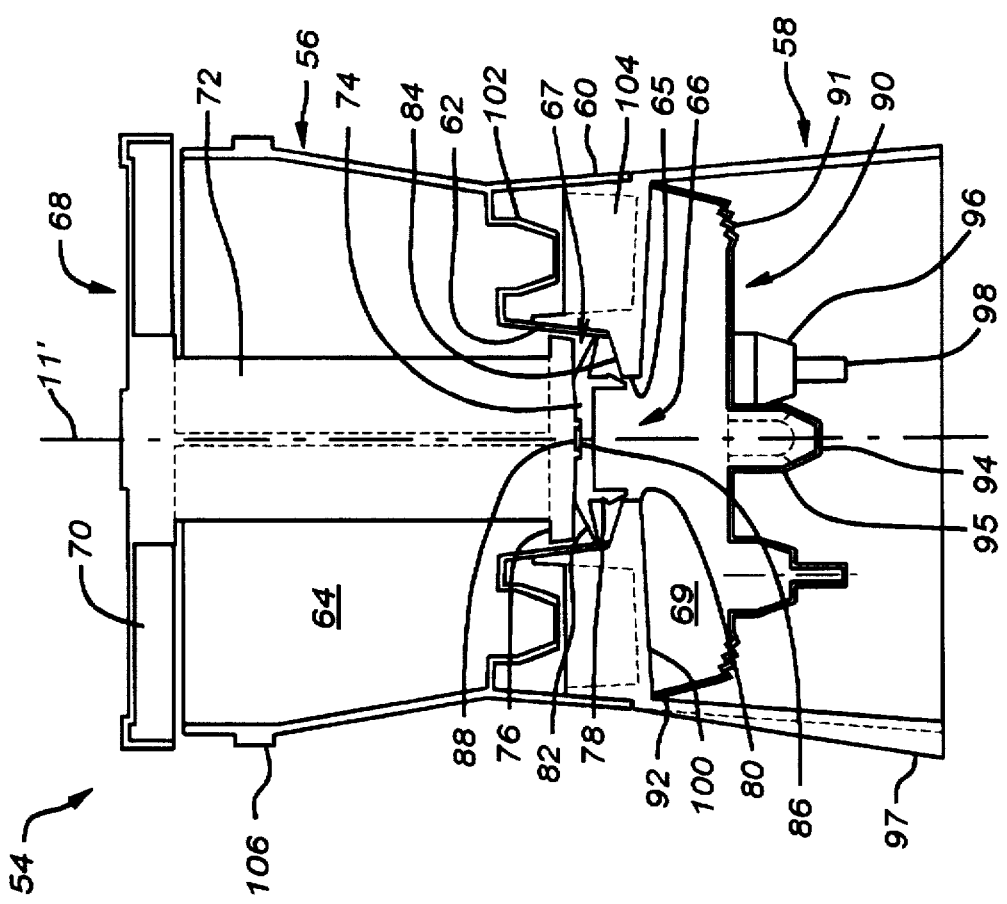
FIG. 2 is a side sectional view of another embodiment of the present invention.
Figure 5B:
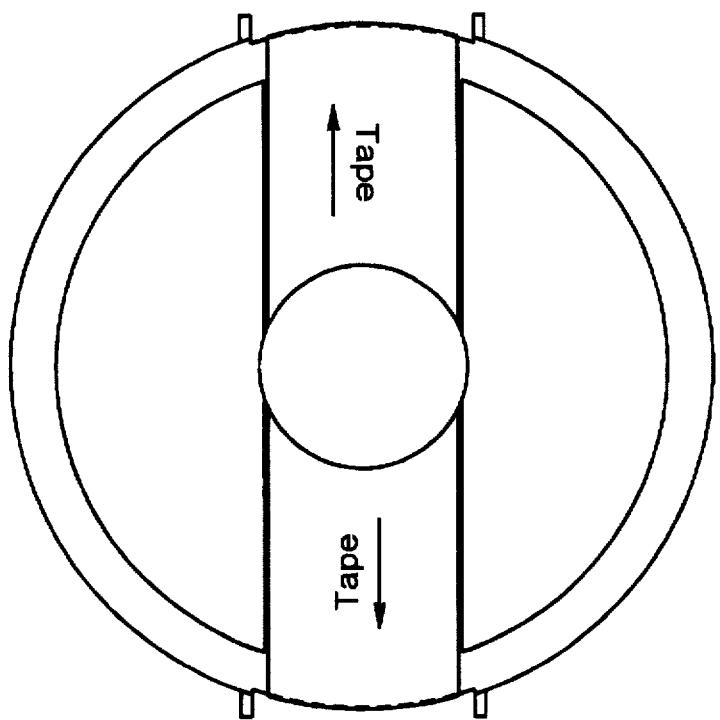
FIGS. 5A is a side sectional view of the embodiment of FIG. 4A showing the recepticle lid in sealing position.
Figure 5A:
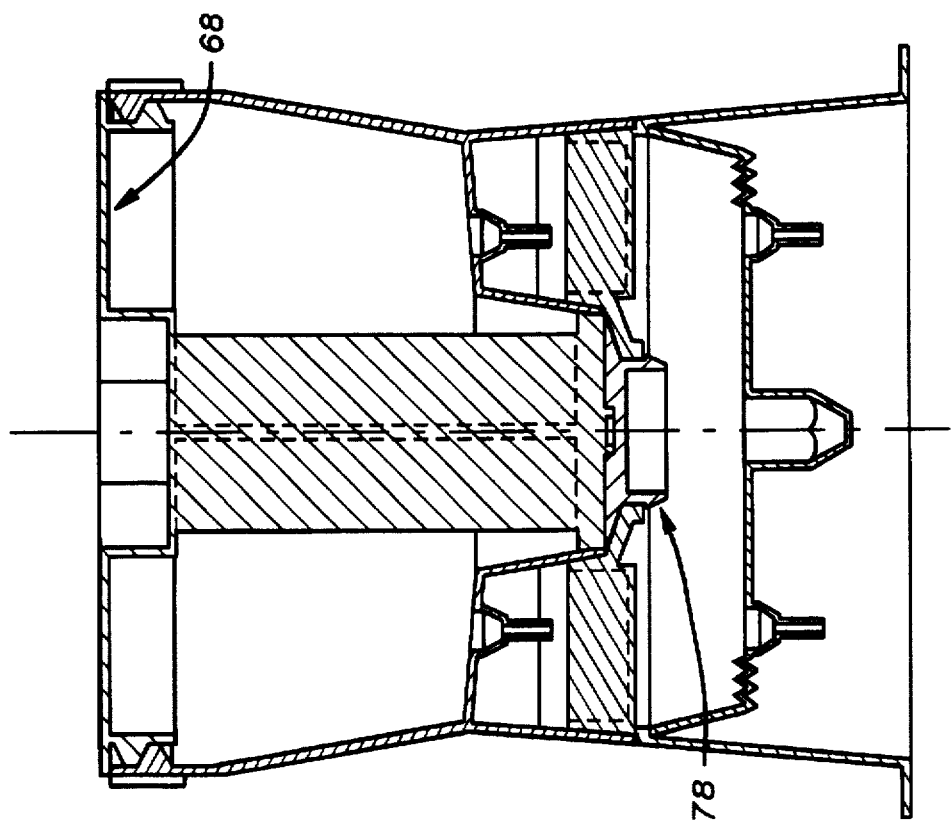

While the foregoing embodiment is suitable, a simpler and more cost effective embodiment is described starting with FIGS. 2 and 3 and comprises a receptacle with no self contained piercing/sampling system. This embodiment is appropriate for use with a testing instrument, which, using hot wire, rotating blades, or other appropriate means, accesses the receptacle and the sample contained within the receptacle. In this way (i.e., the simplification of receptacle geometry and the elimination of separate parts), the cost of the receptacle is reduced. In other words, since most samples test negative, overall cost is reduced if access to the sample contained in the receptacle is provided by a means "off" the receptacle such as, for example, in the instrument that tests the sample.

The (lower) primary sample container is preferably fabricated of a material that, while somewhat deformable, is relatively rigid in structure. Consequently, receptacle transfer from areas of low pressure such as those found in mountainous regions to high pressure such as those found at sea level or below, or the reverse transport, or aviation transport and exposure to high altitude reduced pressures, will cause significant pressure changes that will not be compensated for by the material of the receptacle, or by any appreciable compression by air which may be found in the primary sample container. This possibly can disrupt the sealing mechanisms of the receptacle of this invention and cause leakage. To compensate for pressure effects, the present invention provides pressure equilibration means described below starting with FIGS. 2 and 3.

The physical geometric size and shape of the sample access ports inherently contain surface tension elements which may inhibit the fluid sample from freely flowing from the port. For example, the diameter of the flow port as illustrated in FIG. 1a is such that fluid will flow out of the port and be pressure compensated by air which will replace the freely dispensing sample fluid at regular intervals. In the preferred embodiment of the sample access ports described starting with FIGS. 2 and 3, the diameter of the sample port is small in relationship to its length. In this manner, fluid is inhibited from entering the sample port because of the surface tension of the port and its closed end. To compensate for this surface tension phenomenon, the present invention provides means and a method to "pump" fluid out of the primary sample chamber.

These pump means advantageously are combined with means providing a pressure equilibration mechanism to compensate for the pressure variations described above. Referring to FIGS. 2 and 3, there is provided in the floor of the lower chamber a bellows assembly 90 in which concentric rings 91 are molded as an expansion element. The expansion element may also take the form of a multi-ring spiral. The object is to create a large surface area of the bellows assembly 90 in a small space. As mentioned above, the preferred material of the receptacle is relatively rigid, yet moderately deformable. Consequently, any pressure differential between ambient and the interior of the primary sample container will equilibrate by distention of the volume of the container contained in bellows assembly with the spiral or concentric rings.

Also, a protrusion 94 at the center of the bellows assembly 90 allows for engagement by an instrument. A circumferential bump 95 may be included to assist in mechanically grasping the protrusion 94. By engaging the protrusion 94 and "pulling" down slightly, the pressure within the primary sample container is reduced with respect to ambient pressure, as the volume of the primary sample container is enlarged by this action. Consequently, when an access port is violated, no sample flows. Instead, ambient air enters the primary sample container through this access port in order to equilibrate the pressure between the container and ambient. This action allows the violation mechanism to remain free from potential contamination from the sample inside the receptacle and allows for serial placement of sample cups under the access port, suitably by an operator or the testing instrument. By reversing the direction of the engaging mechanism of the instrument, to upward, the volume of the primary sample container is reduced, and the interior pressure is increased in excess of that required to overcome the surface tension of the access port and sample flows into the cup placed under the access port. When the cup is filled, the engaging mechanism again reverses its direction, downward, and air again enters the primary sample container. This action evacuates the access port so that the sample cup may be removed from under the access port and a mechanism engaged to crimp/heat seal the access port completely and without risk of contamination.

The preferred embodiment of FIGS. 2 and 3, like that of FIG. 1, comprises a bi-compartmented fluid sample receptacle 54, and with the understanding given by the detailed description in relation to FIG. 1, is more simply described. It has an upper compartment or isolated sample chamber 56 and a lower compartment or primary sample chamber 58. The bottom view of lower compartment 58 is shown in FIG. 3. The lower compartment 58 is friction fitted to the upper compartment 56 by an outer circumferential skirt 60 and an inner skirt 62. The upper compartment 56 has a wide aperture 66 at the bottom of chamber 64. The aperture 66 fits into a mating apertured portion 65 of the lower compartment 58 of the receptacle. The aperture 66 is made wide to eliminate fluid surface tension problems in flow of the sample. Fitted together, aperture 66 and apertured portion 65 form a passage 67 fluidly connecting upper chamber 64 and bottom chamber 69.

Shown located above the upper compartment 56 is a lid closure assembly 68 in axial alignment with an axis 11' centered in passage 67 fluidly connecting chamber 64 in upper compartment 56 and chamber 69 in lower compartment 58. The lid closure assembly 68 has threads which are molded around its outside (FIG. 4a) or inside (FIG. 2) periphery, and contains a lip which facilitates the sealing of the device. Suitably, lid cover 70 is threaded onto the upper compartment 56 by internal threads advanced along threads provided exteriorly on the upper wall of compartment 56. The lid closure assembly 68 includes a sealing cover 70, a stem or column 72, and a detachable lower plug seal 74. The lower end of stem 72 terminates in a plug configuration providing an upper sealing plug 76 that, when engaged, seals off the passage 67 from chamber 64. The periphery of upper sealing plug 76 is formed to sealingly mate with the skirt 62. Upper sealing plug 76 and the skirt 62 are of such shape to facilitate sealing engagement as the lid closure assembly 68 is axially moved downward into passage 67, as by pushing sealing cover 70 down on the upper compartment to engage the companion threads in cover 70 and those on the upper compartment 56.

Forcing the lid closure assembly 68 onto the upper compartment 56 by pushing and/or screwing motion also engages the detachable lower seal 74 with the lower compartment 58. A circumferential detent 78 in a downwardly depending flange engages a shoulder 80 in the lower compartment. Simultaneously, a flexing plate 82 bends into sealingly flush alignment with a slanted surface 84 of the lower compartment 58, and held in that position by the engagement of detent 78 on shoulder 80, seals the upper chamber 64.

At the bottom of stem plug 76 in the center a small plug protrusion 88 extends vertically in the axis 11' and may be of any geometric shape. On the outside of this protrusion at least one extension member projects horizontally outward, and may take the form of a continuous ring type band or a plurality of tips. Lower seal 74 has a vertical indentation 86 greater than the length of protrusion 88 and is of a geometric shape such that the plug protrusion fits inside the indentation. Indentation 86 has a horizontal inset ring molded within it (not shown) such that when lower sealing plug 74 is coupled with the top, the extension member such as the tips reside within this inset ring, thereby coupling the stem and terminal upper plug 76 with the lower plug 74. Suitably the protrusion has a plurality (e.g. four or five) tips of suitably about 0.005–0.008" that slide into the channel to engage the lower seal 74. Thus, the devices may be separated with a slight to moderate amount of force which will be proportional to the number of tips on the protrusion 88 of the top plug. This detachable engagement permits disengaging the upper and lower compartments while maintaining each of the compartments independently sealed and allows for conventional molding techniques.

A diaphragm or bellows assembly 90 is heat sealed to a molded ridge 92 on the inside surface of the lower compartment 58. This heat seal is preferably formed by friction heat by spinning the bellows assembly 90 and the lower compartment 58 relative to one another. This seal may also be formed by ultrasonic welding as in the embodiment depicted in FIG. 1 or sealed using a chemical solvent. Thus, the lower compartment corresponds to the base 14 of FIG. 1, while the bellow assembly 90 corresponds to the floor lower retaining well 16 and retains the fluid sample.

Depending from the center of the bellows assembly 90 is a center guide nipple 94, preferably multi-angular, circular, or a combination (such as square with rounded corners) in cross-section. A female receptor (not shown) on a testing/ sampling instrument grasps the guide nipple 94 to begin the analysis process for the fluid contained within the receptacle 54.

A plurality of sampling nipples 96, placed circumferentially about the center guide nipple 94, downwardly depend from the lower side of the bellows assembly 90. Each nipple 96 includes a relatively thin protrusion 98 that provides a fluid discharge path for fluid analysis, as described below. Spaced about the periphery of the lower compartment are a plurality of elongated tines or keys 97 that allow alignment of the receptacle 54 with the testing/sampling instrument. Alternatively, the polarizing or alignment keys may take the form of horizontal tabs which extend radially outward from the base of the lower container.

In operation, a sample donor provides a fluid sample (such as urine) into the top of the upper compartment 56. The fluid flows through the aperture 66 into the lower compartment 58, contained by the bellows assembly 90. The fluid level rises to a height 100 within the bellows assembly defined by the shoulder 80 of the lower compartment. The fluid level continues to rise, now within the upper compartment to a level at a height to lake above the plurality of standard nipples 102 in the upper compartment 56. Then the lid closure 68 is screwed on, forcing down the seal 74 and the plunger 76 to seal off the upper and lower compartments.

When the receptacle arrives at the laboratory testing site, an accepting device on a testing instrument (not shown) grasps and accepts the center nipple 94. The accepting device pulls down on the center nipple 94, thus drawing down the bellows assembly 90, thereby creating or increasing the vacuum in the chamber 69. A fluid withdrawal tool then engages a first of the protrusions 98 and clips, violates, or cuts it off, permitting air to rush into the bellows assembly 90 by way of the protrusion 98 and the nipple 96, bringing the pressure within the bellows assembly 90 to atmospheric. The testing instrument then pushes upward, to develop a positive pressure within the bellows assembly to force a portion of the fluid sample to flow out the severed protrusion 98. Thus, the bellows assembly serves at least the two functions of accommodating changes in ambient pressure around the receptacle and facilitating expulsion of the fluid sample from the lower compartment.

The sample from the lower compartment is expelled into a sample cup (not shown), where suitably an infrared sensor (not shown) detects the level in the sample to determine a precise volume of the fluid sample to be tested. When this is done, the protrusion 98 is heated or mechanically sealed and thus the nipple 96 is closed to prevent leakage of fluid remaining in the lower compartment. In this way, a portion of the fluid sample remains within the lower compartment. If confirmation of the results of the testing of the first fluid portion is required, the testing instrument can index the receptacle (such as by use of the protrusion 94) to engage the protrusion 98 of another nipple 96 to take a backup portion of the fluid within the lower compartment. For each sample to be tested, the bellows assembly 90 acts as a pump to force fluid out of the lower compartment.

If the results of the sampling and testing by the first testing facility are questioned or challenged, the upper and lower compartments may be separated (while each maintains a sealed sample within) by gently rocking the upper and lower compartments relative to one another. The rocking force required is more than a sample receptacle would normally experience in transit or through normal handling but is slight enough to easily permit separation of the compartments. The compartments separate at the junction of the indentation 86 and the protrusion 88. Then, the upper compartment with a fluid sample contained therein is sent to another testing lab to confirm the results of the first tests. At the second testing lab, fluid sample is withdrawn from the upper compartment by way of one of the nipples 102. Thus, the upper compartment serves at least the two functions of directing the fluid sample into the lower compartment and as a container for a redundant sample for further testing.

In use, after a fluid sample is taken and the lid 68 is installed, a length of security tape is installed at the upper seam formed by the lid 68 and a shoulder 106 on the upper compartment to provide a positive means of indicating if the sample has been tampered with.

The receptacle depicted in FIGS. 2 and 3 simplifies the embodiment of FIG. 1. For example, the receptacle of FIGS. 2 and 3 eliminates the need for cap sleeves 22 and the relatively complex shape of the flow guides 20. The sealing feature on the lower end of the column 72 is both simpler to mold and provides a more positive seal than the plug arrangement at the lower end of the column 30. Finally, although simpler in construction and manufacture, the embodiment of FIGS. 2 and 3 provides a bellows assembly 90 accommodate changes in ambient pressure and as a positive means of expelling sample fluid from the receptacle, features not provided by the embodiment of FIG. 1.

FIGS. 4A, 4B, 5A, and 5B depict a preferred embodiment of the present invention before and after the installation of a closure lid 68. The arrangement of the receptacle of these figures is substantially similar to that of FIGS. 2 and 3 with certain additions. First, a plurality of nipples 110 on the isolated sample chamber 56 mirror the nipples 96 of the primary sample chamber. This way, a sample fluid in either of the upper and lower sample chambers may be sampled in the same type of automatic sampling/testing device. This also provides an additional guard against human error in handling and analyzing test samples.

The lid 68 includes a pair of recesses 112 along its periphery. As shown by the arrows in FIGS. 4B and 5B, the recesses 112 serve as guides for the installation of tamper resistant tape once a sample is taken and the lid 68 is installed. In this embodiment, the shoulders 106 serve the additional function of indicating that the lid is in its fully inserted position and extend the recesses 112 to guide the tamper evident tape.

FIGS. 6A through 6D depicts another preferred embodiment of the present invention. In this embodiment, a lower seal 120 is constructed as a portion of the lower sample chamber assembly. In this case, it is no longer "detachable" from the column 72 (FIG. 6A) as in previous embodiments.

Figure 6E:
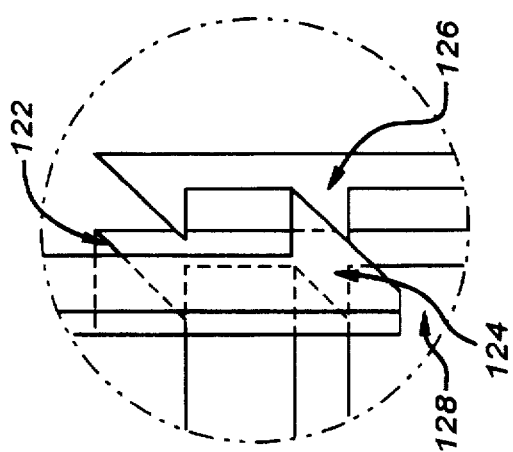
FIG. 6E is a zoom view of a portion of the plug stem illustrating a configuration for retaining the stem in presealing position.
Figure 6B:
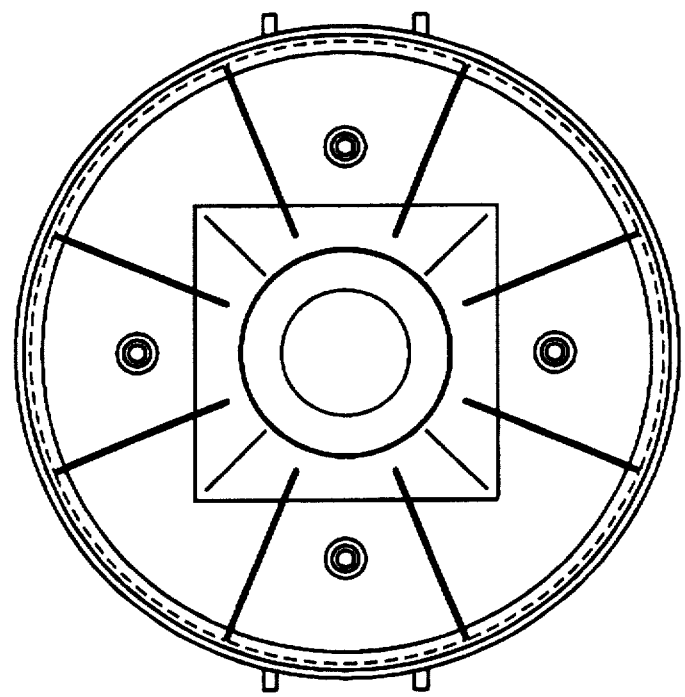
Figure 6A:
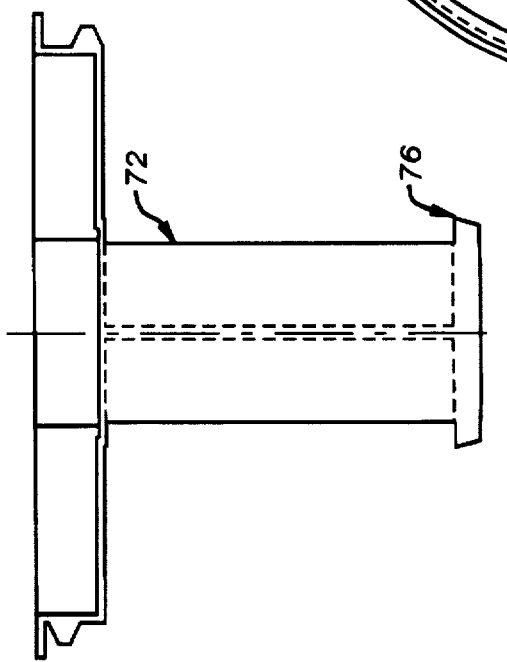

FIG. 6C illustrates the bi-compartmented sample container with the closure lid 68 in place. The plunger 76 has abutted and forced down on the lower seal 120, driving the lower seal 120 into sealing engagement with the lower or primary sample chamber. Since the column 72 and plunger 76 are not attached to the lower seal 120, no effect is required to separate them as the upper and lower sample chambers are separated. This eliminates a possible problem in the lower seal 120 becoming detached from the plunger 76 before the lid closure 68 is installed.

FIG. 6D depicts the sample container before the closure lid 68 is installed. The lower seal 120 includes a lower extension 122. The lower end of the extension terminates in an annular rim 124 which resembles a sawtooth in cross-section. The annular rim 124 abuts a support ring 126 by force of gravity until the closure lid 68 with its attached plunger 76 is put in place. Then, the plunger abuts the top of the seal 120, the annular rim 124 rides over the support ring, and the rim 124 and extension 122 slide down into a cylinder 128 within the now hollow protrusion 94. The plunger 76 continues down until the seal 120 in sealed into place.

Note that the seal 120 and extension 122 assembly (which is preferably a single molded element) is inserted into the cylinder 128 during assembly at the factory after the upper and lower sample chambers are attached to one another.

One feature of the embodiment of FIGS. 6A–6D that is equally applicable to other embodiments is a top wall 130 of the primary sample chamber. The top wall 130 in this embodiment is substantially level or it may even slant upward toward the axis 132 of the container. This structure eliminates the void 104 (FIG. 2). Eliminating the void 104 may in certain circumstances minimize or even eliminate flexing cycles of the bellows assembly 90 and eliminate some of the fatigue in some of the structural elements of the receptacle.

Figure 7C:
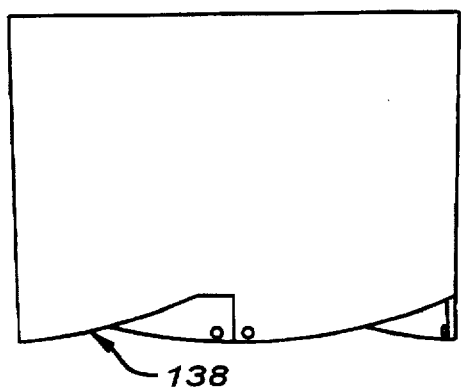
FIGS. 7 and 8 depict stylized side walls of sample containers of the present invention showing preferred interface surfaces between upper and lower sample elements.
Figure 8C:
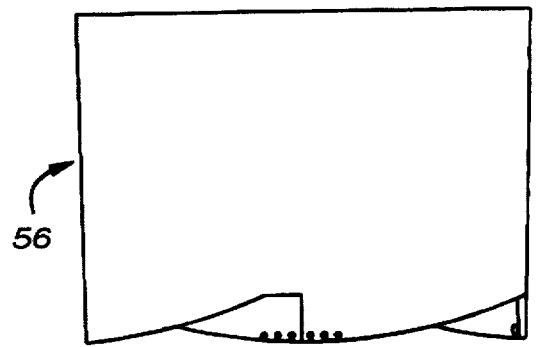
Figure 7B:
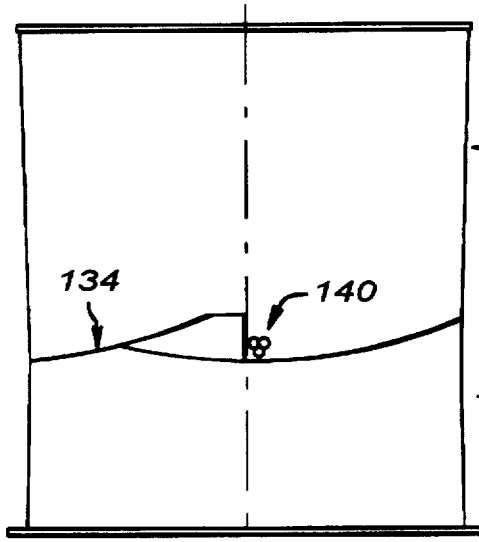
Figure 8B:
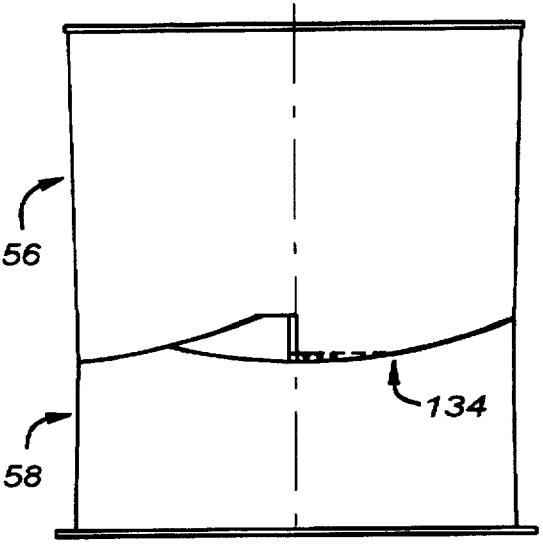
Figure 7A:
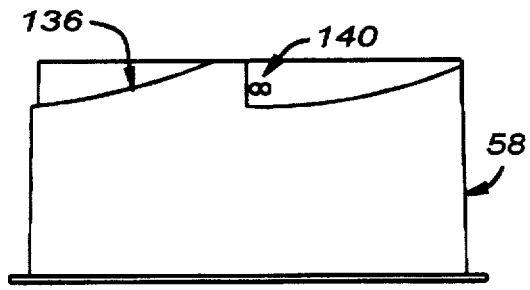
Figure 8A:
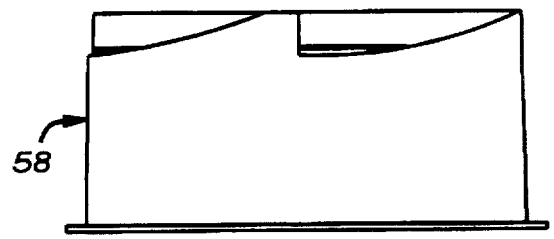

FIGS. 7 and 8 depict an additional feature that is adaptable to any of the embodiments previously described. The upper or isolated sample chamber 56 and the lower or primary sample chamber 58 meet together at a seam 134. At the seam 134, a lower edge 136 of the isolated sample chamber 56 and an upper edge 138 of the primary sample chamber 58 meet in an inclined plane. This structure provides the advantage of imparting a controlled amount of axial thrust when the upper and lower chambers are rotated relative to one another when the chambers are to be separated.

The upper and lower sample chambers are releasably held together by, for example but not by way of limitation, by a set of cooperating bumps and detents 140. These cooperating elements hold the upper and lower sample chambers against normal against normal abuse to be expected during transport and handling during sampling procedures. However, they are releasable by action of torsion stress between the chambers.

Referring to FIGS. 9a–9F, FIGS. 10a–10f and FIG. 11, a liquid specimen collection container indicated generally by reference numeral 200 comprises an upper sample chamber 202 having an upper access opening 204, a lower sample chamber 206 releasably engageable with the upper sample chamber 202, a flow passage 208 connecting upper chamber 202 and lower chamber 206 to conduct liquid from the upper sample chamber 202 to the lower sample chamber 206, and a container closure and seal generally indicated by reference number 210, engageable with the upper sample chamber 202 to close upper access opening 204 and seal upper sample chamber 202 and lower sample chamber 206 adjacent the flow passage 208.

Figure 9A:
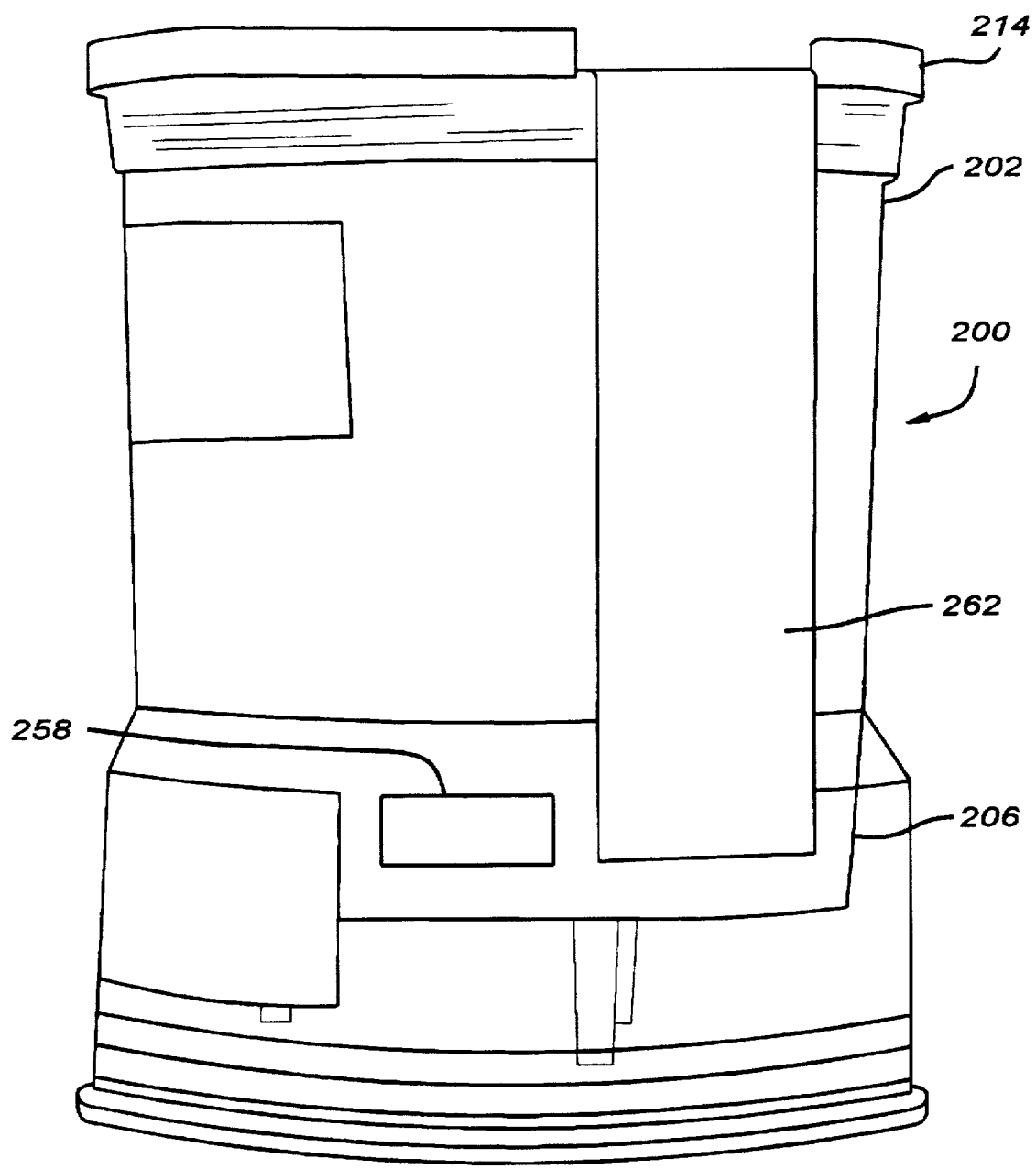
FIG. 9a is side perspective view of an assembled specimen collection container of this invention.
Figure 9B:
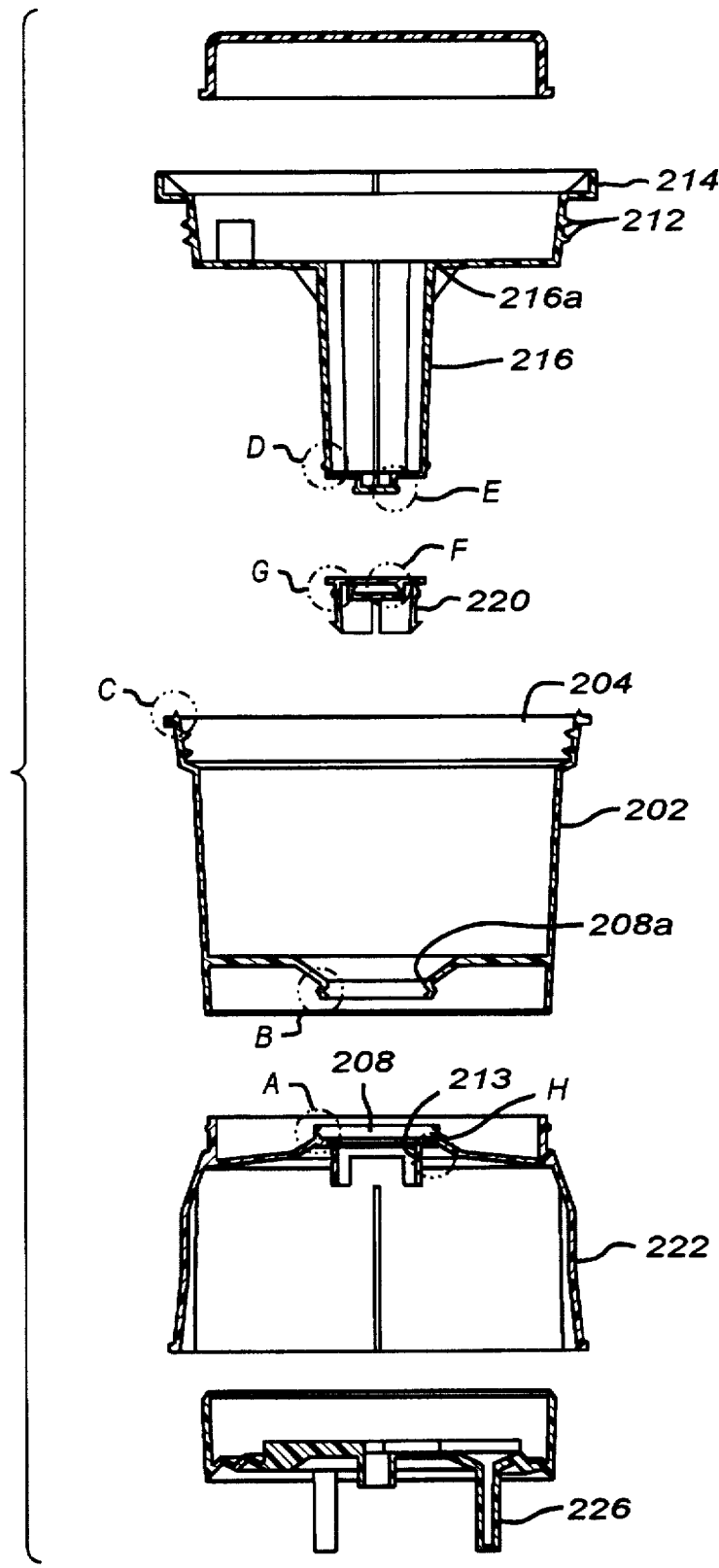

Suitable "bumps and detents" means for releaseable engagement of lower sample chamber 206 with the upper sample chamber 202 are shown in FIG. 9b, at the zoom details legended by reference letters A and B. Zoom detail A (FIG. 9Fi) shows an annular groove 201 is provided in the peripheral interior wall of a neck 223 in a base 222. In zoom detail B (FIG. 9Fii), an annular rib 203 is provided in the external wall of neck 249 of 208. Rib 203 snaps into groove 201 and releasably connects upper chamber 202 to lower chamber 206.

The container closure or top 210 comprises a lid 214, sealingly engageable with upper sample chamber 202, suitably as by exterior threads 212 on lid 214 and interior threads on chamber 202. Zoom detail C in FIG. 9b (see FIG. 9Fiii) shows a secondary or assist means of securing closure of top 210 with upper chamber 202. A triangular ring 205 of the plastic material with which chamber 202 is molded is provided at the rim 207 of upper access opening 204. When top 210 is screwed down and presses onto ring 205, an intimate plastic weld is setup for cold flow bonding.

Container closure 210 further comprises (i) a vertical column 216, suitably strengthened by vertical ribbing 209, joined to lid 214 at a first end 216a of the column, (ii) an upper plug portion 218 of the column at a second end 216b of the column sealingly engageable with upper sample chamber 202 adjacent passage 208 in an upper portion 208a thereof, and (iii) a lower plug 220, releasably joined to the upper plug portion 218 to seal the lower sample chamber 206.

Zoom details D (FIG. 9Fiv) and B (FIG. 9Fii) illustrate means by which upper plug portion 218 sealingly engages upper sample chamber 202 adjacent passage 208 in upper portion 208a. An annular groove 209 is provided in the peripheral interior wall of a neck wall of neck 251 of 208. An annular rib 211 is provided in the external wall of upper plug portion 218. Rib 211 snaps into groove 209 and sealingly connects upper plug portion 218 to upper sample chamber 202.

Zoom details E (FIG. 9Fv), F (FIG. 9Fvi), G (FIG. 9Fvii) and H (FIG. 9Fviii) show means by which lower plug 220 is releasably joined to the upper plug portion 218 to seal the lower sample chamber 206. Referring to FIG. 9Fviii (Zoom H) a collar 213 in base 222 comprising a portion of flow passageway 208 includes an annular groove 215 in the peripheral interior wall of collar 213. Referring to FIG. 9Fvii (Zoom G) a annular rib 217 is provided in the external wall of lower plug 220. Rib 217 snaps into groove 215 and seals lower plug portion 220 to seal the lower sample chamber 206. Referring to FIG. 9Fiii (Zoom E) an annular rib 219 is provided in the external wall of the base of the upper plug 218. An annular groove 221 is provided in the peripheral interior wall of a recess matingly receiving a tip portion of upper plug 218. Referring to FIG. 9Fvi (Zoom F), rib 219 snaps into groove 221 and releasably joins lower plug 220 to upper plug 218.

Lower sample chamber 206 comprises a base 222, a variable volume bellows assembly 224 joined to base 222, at least one and as illustrated preferably a plurality of access apertures or nozzles 226 in a lower portion of bellows assembly 224, and a retaining element 228, suitably in the form of an annular keeper groove 215, to cooperatively engage a mating element 230, in the form of a projecting annular rim 217, on lower plug 220. A guide recess 232 is formed centrally in the underside of bellows assembly 224. Suitably the lower sample chamber 206 has a volume of about 33 mL, and when filled will hold about 30 mL of liquid specimen and captured by the shape of the roof of base 222, about 2 to 3 mL of air.

Figure 10D:
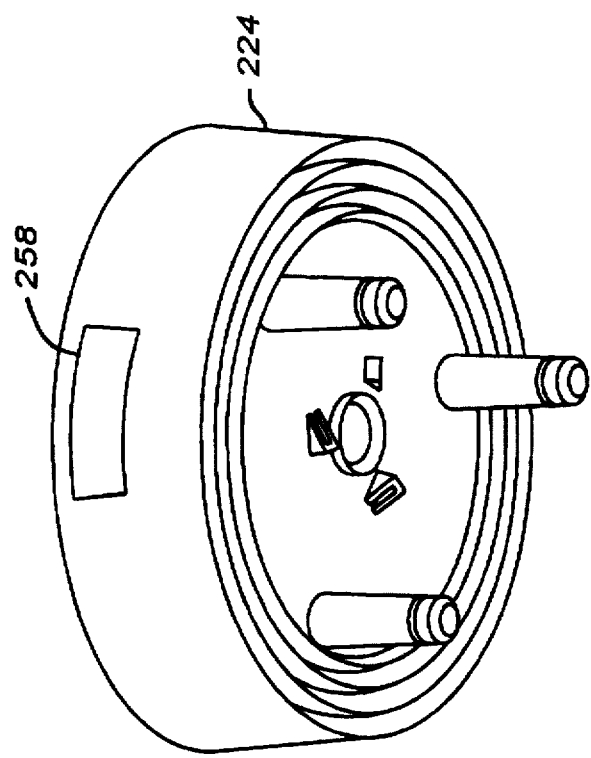
Figure 10C:
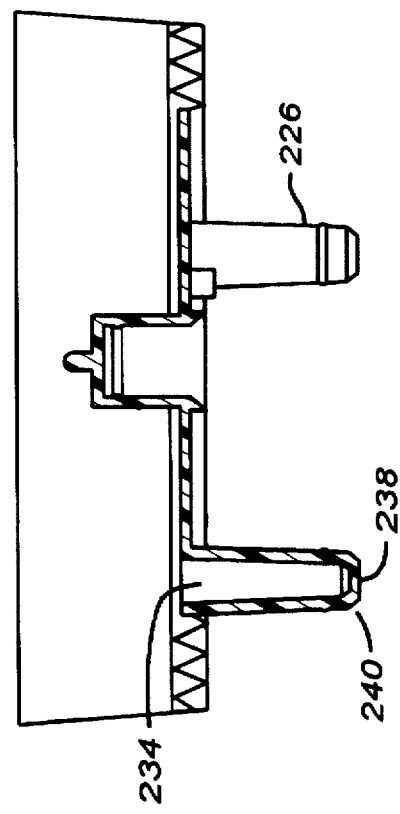
Figure 10F:
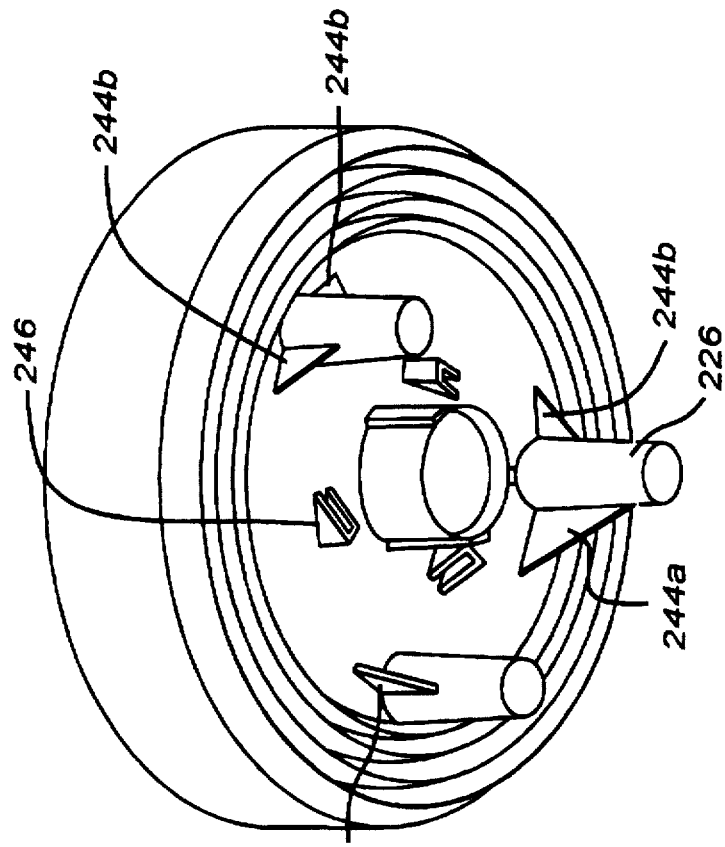
FIG. 10f is a bottom perspective view of a modified primary collection chamber bellows assembly device of FIG. 10d.

The three nozzles 226 illustrated are spaced 120 degrees apart. The nozzles have a duct 234 opening into lower sample chamber 206 of container 200, and also have a closure 238 closing the duct remotely from the duct opening into chamber 206. Closure 238 may be at the tip 240 of the nozzle as shown in FIG. 10c and FIG. 10g, or may be positioned between the duct opening to chamber 206 and the nozzle tip as indicated at 242 in FIG. 10g. Nozzles 226 may additionally have flag structure 244 to distinguish between a primary nozzle and secondary nozzles. Referring to FIG. 10f, one nozzle 226 has a larger flag structure 244a than a similar such structure 244b on the other two of nozzles 226. Structure 244 may be on only one nozzle. The structure suitably may be any shape that does not interfere with the function of the elements of container 200.

On the underside of bellows assembly 224, three ramp ears 246 are equally spaced between nozzle ports 226. A plurality of upstanding ribs or vanes 248 radiate from the periphery of guide recess 232 to an upstanding annular tie 250 radially inward of a bellows portion 252 of bellows assembly 226. A floor plate portion 254 of the bellows assembly is radially inward from bellows portion 252. The interconnection of the periphery ring 231 of recess 232 and the annular tie 250 with vanes 248 provides additional rigidity to the floor plate of bellows assembly 224.

A temperature crystal 258 may be glued to the exterior of bellows assembly 224. A tamper evident seal 262 may be placed over lid 214 onto the outside of upper and lower sample chambers 202 and 206, and another seal may be placed across the mouth 264 of base 222 over rim 223.

The portion of container 200 not including the container closure 210 is generally indicated by reference numeral 270 in FIG. 9c.

Figure 11B:
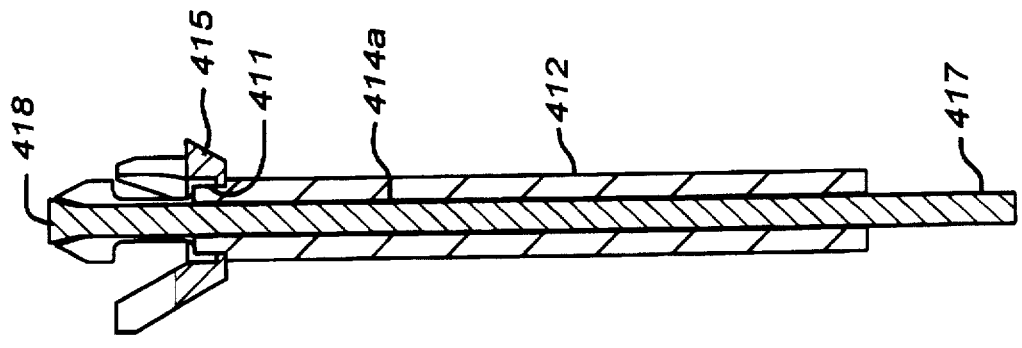
Figure 11A:
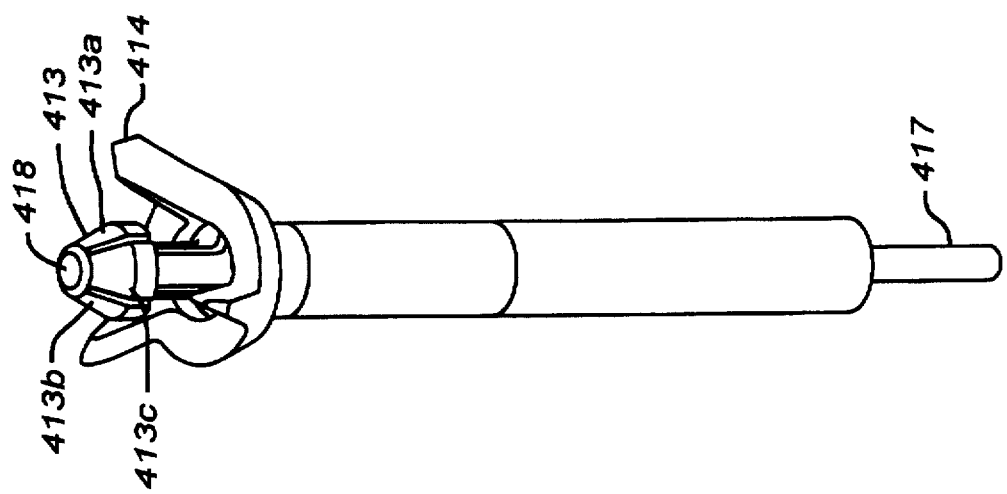
FIG. 11a is a perspective view of a device suitable for use in connection with the containers of FIGS. 9a–10g.

Referring now to FIGS. 11a-b, illustrated is a device suitable for gripping container 200. A driver/gripper piece 412 comprises a collet grip head 413 and a three pronged drive dog 414. Collet grip head 413 comprises four projections 413a, 4136b, 413c, 413d extending upwardly about a central bore 414a of an annular base portion 415 surmounted and fixed on shoulder 411. Passing through central bore 414a of piece 412 is a pull rod 417. The distal end of pull rod 417 has an enlarged radius portion 418. The most distal interior surfaces of collet gripper projections 413a, 4136b, 413c, 413d at the opening to central bore 414a are chamfered to permit pull rod enlargement 418 to be retracted into central bore 414a. Retraction of pull rod enlargement 418 spreads projections 413a, 4136b, 413c, 413d radially outward from central bore 414a.

In the use and operation of container 200, at a place of specimen collection a container in the partially assembled state shown in FIG. 9c is removed from a sealed wrapper. In a typical chain of custody procedure, the donor, after completing a multicopy requisition, is given the container portion 270 of the assembly. The collector retains the container closure 210. The donor privately urinates into the container portion 270 through upper access opening 204. Urine flows from upper sample chamber 202 into lower sample chamber 206 through flow passage 208. Lower sample chamber 206 fills, then upper sample chamber 202. The shape of the roof of lower chamber 206 assures very little air is trapped in the lower chamber as urine fills it and rises through flow passage 208 to occupy upper chamber 202. The donor returns the container 270 to the collector, who closes the container using closure 210. Closure 210 seals lower chamber 206 from upper chamber 202. The intrachamber pressure is the same as the ambient pressure of the situs of collection. The collector reads temperature indicator 258 to verify that the specimen is at body temperature (an authentic undiluted specimen) and places a tamper evident tape 262 across lid 214 and onto the sides of the container (FIG. 9a). The donor initials tape 262. The taped container is placed in one compartment of a two compartment mailing pouch. The requisition is signed by the donor and collector, a copy of it is given to the donor and a file copy is retained by the collector. The remainder of the requisition is placed in the second compartment of the pouch. The pouch is then sealed and delivered to the testing laboratory, where a sample or aliquot of the specimen in the container will be removed for analytical testing. The bellows assembly 224 of container 200 permits lower chamber 206 to expand upon exposure of the container to any materially lower ambient pressure either during transit or at the destination site. Conversely, the bellows assembly 224 of container 200 and the small amount of air permitted captured by the roof of lower chamber 206 during chamber filling permit lower chamber 206 to contract upon exposure of the container to any materially higher ambient pressure either during transit or at the destination site. Bellows assembly 224 therefore assures that the ambient pressure changes to which the container is exposed do not cause the container to leak.

At the destination, the testing laboratory continues assurance of chain of custody of the container. A technician removes the container and the requisition from the pouch and attaches identical bar code labels from a set, one to the requisition, one to the upper half of the container and another to the lower half of the container. The label on the upper half assures that identification of the specimen in the upper half is the same as in the lower half. A batch of containers similarly handled and labeled is gathered for processing in a batch operation, typically a batch of 40 containers.

Figure 12C:
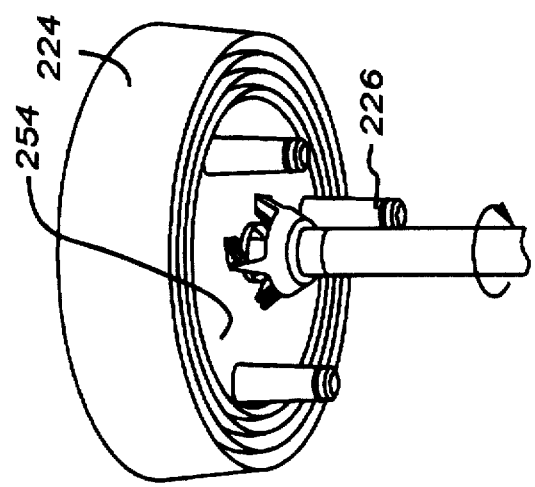
FIGS. 12a–12c are bottom perspective views illustrating an interaction of the device of FIGS. 11a–11b and a container portion illustrated in FIGS. 9a–9d.
Figure 12B:
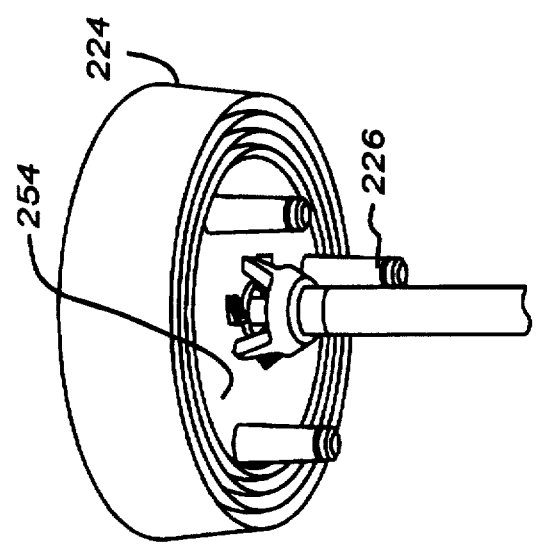
Figure 12A:
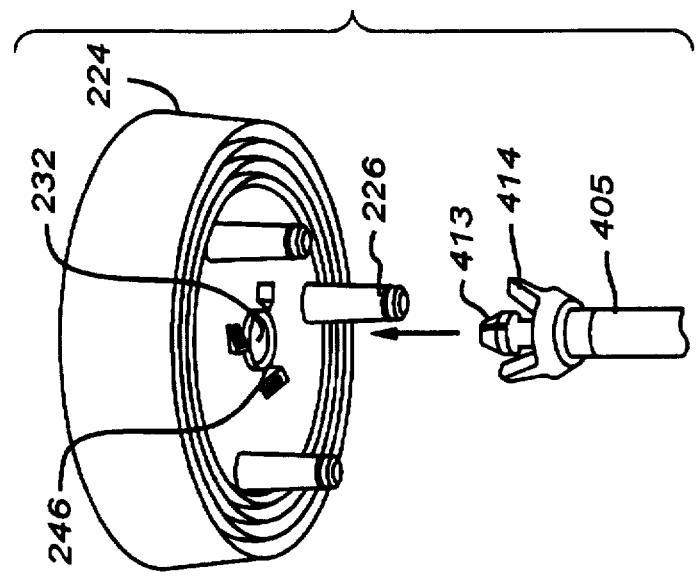

Referring to FIGS. 12a-c, collet grip head 413 and three prong drive dog 414 rotatingly axially spiral up and collet grip head coaxially enters guide recess 232. The correspondingly moving prongs of drive dog 414 spiral upwardly at a horizontal vector less acute than the ramp incline of ears 246. Upon entry into guide recess 232, collet grip head 413 ceases vertical travel. Then collet grip head 413 is rotated a predetermined extent, more than 90 degrees and less than 180 degrees of rotation, suitably 140 degrees, to assure drive prongs 414a, 414b and 414c are firmly engaged with the vertical side of ramp ears 246 on the underside of bellows assembly 224. Then pull rod enlargement 418 is retracted, radially spreading collet head 413 in guide recess 232, thereby gripping container 200. Collet grip head 413 then rotates to spin container 200 two full turns. As container 200 spins, a container bar code reader reads the bar code label on the lower sample chamber. Because the first part of the bar code could be already past the bar code reader when container 200 commences rotation and the reader commences reading, container 200 is spun twice to give at least one full bar code label passage across the bar code reader to assure the reader begins a read at the start of the bar code label.

As container 200 is spun, elevationally staggered optoelectric sensors can detect whether any of the nozzles 226 sweeping by them do not have the length required to interrupt the lower of the two sensors. This checks whether any nozzle has a tip that will not be at an elevation expected. For example, a differential in length may occur where a container 200 previously has been accessed through a nozzle by truncating a nozzle tip to take a sample of the specimen. Alternatively, if a nozzle has structure 244a to identify it as a primary nozzle, as illustrated in FIG. 10f, the optoelectric sensors may be situated to read the passing nozzles for the presence or absence of the distinguishing structure. One revolution plus a few degrees is all that is required to read the nozzles, and the requirement is more than satisfied by the two revolution spin for the bar code label read. Passing the nozzles by elevationally staggered optoelectric sensors therefore optionally can discriminate among the nozzles to deselect a nozzle or select a nozzle for opening.

Figure 10E:
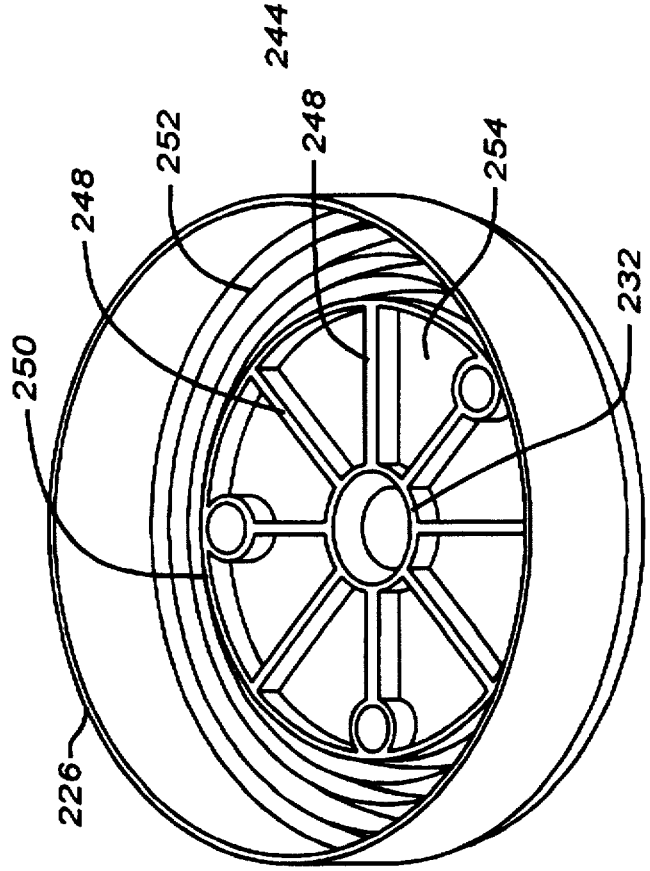

The spin of container 200 also serves to agitate the specimen in chamber 206 of container 200. The agitation and a resuspension of any sediment in the specimen in chamber 206 is aided by vanes 248 in the floor of chamber 206 (FIG. 10e).

Then collet grip head 413 rotates container 200 to place a located and selected (or not deselected) nozzle 226 in coaxial alignment with the fixed focal point of a laser beam. The bellows assembly feature of container 200 has automatically adjusted the volume of chamber 206 since sealing to prevent any pressure differential between the interior of chamber 206 and ambient pressure. A negative intrachamber pressure relative to the ambient pressure is suitably now induced by increasing the distance between the top and bottom of chamber 206. Collet grip head 413 is lowered to pull down floor plate 254 of bellows assembly 224 relative to base 222 of lower sample chamber 206 and increases the volume of lower sample chamber 206. Because chamber 206 is sealed, this increase in chamber volume reduces the intra-chamber pressure relative to ambient pressure. Vanes 248 in interconnection with recess periphery ring 231 and annular tie 250 provide structure and additional rigidity to the floor plate of bellows assembly 224, and this furnishes additional assurance that bellows assembly 224 pulls down essentially horizontally, maintaining nozzles 226 in a substantially vertical orientation and retaining the placed nozzle 226 in substantial coaxial alignment with the fixed focal point of a laser system suitable used to open nozzle 226.

A laser system or suitably also a pencil column of heated air may be used to open nozzle 226 non-invasively. A non-invasive opening assures that nothing which can carry a contaminant is brought into contact with the specimen during the closure opening procedure. Thus by non-invasively creating a hole in the nozzle closure, the integrity of the specimen in container 200 is preserved.

In using a laser system, a laser lens is centered in a laser beam axis to focus the focal point of the lens on the closure 238 of nozzle 226 placed in coaxial alignment with the laser beam axis. A laser beam shutter is then moved out of the laser beam path and the laser is powered. With the shutter open, the laser emits a beam which is focused by the laser lens onto nozzle closure 226. The laser energy heats the nozzle closure and melts an opening in the closure. The opening of the nozzle closure breaches the means of maintaining the pressure differential created by the pull down of bellows assembly 224. Ambient air at higher pressure rushes upwardly into the nozzle opening and into the nozzle duct and chamber 206 to equilibrate pressure. This influx of gas and any bubbles formed in the duct by the entering air prevents immediate release of liquid from opened nozzle 226. Preferably the ratio of the pierced opening diameter to the length of the nozzle duct is maintained sufficiently small also to contribute to resistance of liquid flow from the opened nozzle.

Referring to FIG. 10g, the tip of nozzle 226 includes a terminal closure. Closure is stepped to provide an axially centered closure membrane portion 238a of lesser thickness than the shoulder portion 238a. The thickness of the membrane portion is suitable to permit a melt through by the laser beam faster than through the step remainder. By coordinating the wattage of the laser and the duration of opening of the laser shutter, melt through will be accomplished only if the center portion of closure is axially aligned with the laser beam. If there is misalignment placing the nozzle tip off center, the laser beam will not penetrate the thicker peripheral parts of the closure and surrounding tip periphery. This assures that an opening is not made off center or eccentrically in the tip closure, for an off center hole could spray a specimen other than in an aliquot receptacle vertically below the nozzle tip. This could contaminate laboratory equipment with the specimen and possibly cross contaminate or adulterate another specimen brought into contact or exposed to an aerosol of the contaminant caused by vaporization.

The closure of nozzle 226 need not be at the tip of the nozzle. As shown in FIG. 10*h*, the closure may be located deep within the nozzle duct. The nozzle configuration of FIG. 10*h* also provides the advantage that in the step of expelling an aliquot of sample from the container 200 into an aliquot receptacle the top of which is not above the tip, the length of nozzle skirt around the nozzle duct below the hole made in the closure 226 by the laser minimizes any lateral expulsion of specimen that might escape the aliquot receptacle.

After an exposure time of 250 to 450 milliseconds, laser shutter is across the beam and the laser is powered down. Then collet grip head 413 rotates container 200 from alignment of opened nozzle 226 over the laser until opened nozzle 226 is disposed over an aliquot receptacle. At the same time collet grip head 413 further pulls down floor plate 254 of bellows assembly 224, assuring that no inadvertent distance closing movement occurs between collet grip head 413 and the roof of chamber 206 that could possibly reduce volume in the primary chamber sufficiently to expel some liquid from the chamber during the rotation of opened nozzle 226 to alignment over the aliquot receptacle. Thus the bellows assembly feature of container 200 also provides the benefit of means for reduction of specimen cross contamination of other specimen samples even with the the nozzle tip open and pointing vertically downward.

Collet grip head 413 and thereby the floor plate of bellows assembly 224 is then vertically elevated a predetermined distance. The upward movement of collet grip head 413 pushes the floor plate of bellows assembly 224 upwardly toward the roof of chamber 206, reducing the volume of chamber 206. The liquid specimen in the chamber is incompressible. The extent of upward travel of collet grip head 413 is predetermined relative to the volume of liquid in the chamber to expel a predetermined volume of liquid from the chamber through the opened nozzle tip.

Collet grip head 413 is then rotated to reposition the open nozzle 226 in the axis for the laser beam. The laser shutter is moved out of the laser beam path, and the laser is powered up. This time the laser lens is not placed in the path of the laser beam. With the shutter open, the laser emits a beam onto nozzle 226. The shutter opens for 250–400 milliseconds. This time the laser beam is unfocused and strikes the tip periphery of nozzle 226 as an unfocused column, melting the nozzle tip periphery. The lens shutter is then closed for about 400 milliseconds and reopened. The cessation of beam energy while the shutter is closed allows the nozzle tip melt to flow across the tip opening. The second hit of energy fuses the closure shut. After about another 400 milliseconds, the lens shutter is then closed again.

Push pull rod 417 is then moved back to home position, allowing laterally displaced grip head projections 413*a*, 413*b*, 413*c* and 413*d* to return to home position and release the grip of collet grip head 413 on container recess 232.

The principles, preferred embodiment and mode of operation of the present invention have been described in the foregoing specification. The invention is not to be construed as limited to the particular forms disclosed, since these are regarded as illustrative rather than restrictive. Moreover, variations and changes may be made by those skilled in the art without deporting from the spirit of the invention.

We claim:

1. A fluid sample receptacle comprising:
   a. an upper sample chamber having an upper access opening;
   b. a lower sample chamber releasably engaged with the upper sample chamber, said lower sample chamber including a variable volume bellows and a closed openable access aperture;
   c. a flow passage connecting said upper and lower chambers to conduct fluid from the upper sample chamber to the lower sample chamber; and
   d. a receptacle closure and seal, engageable with the upper sample chamber and with the receptacle adjacent the flow passage to close and seal said upper access opening and to close and seal the flow passage.

2. The receptacle of claim 1 wherein the receptacle closure and seal comprises:
   a. a lid, sealingly engageable with the upper sample chamber;
   b. a vertical column having first and second ends and joined to the lid at the first end of the column; said second end of the column comprising an upper plug sealingly engageable with the upper sample chamber adjacent said passage; and
   c. a lower plug, releasably joined to the upper plug to seal the lower sample chamber.

3. The receptacle of claim 2 wherein the lower sample chamber includes a shoulder to engage a detent in the plug.

4. The receptacle of claim 2 wherein the lid includes a tape-guide recess.

5. The receptacle of claim 1 further comprising a guide nipple on the bellows assembly.

6. The receptacle of claim 1 wherein said access aperture comprises a severable protrusion discharge nipple.

7. The receptacle of claim 1 wherein the upper sample chamber includes a discharge nipple.

8. The receptacle of claim 1 wherein the upper sample chamber includes a tape guide shoulder.

9. The receptacle of claim 1 wherein the upper sample chamber includes a plurality of tape guide shoulders.

10. The receptacle of claim 1 wherein the upper chamber has a lower edge and the lower chamber has an upper edge that matingly abuts the lower edge of the upper chamber on an inclined plane.

11. A fluid sample receptacle, comprising:
    a. a lower chamber having an upper opening,
    b. an upper chamber releasably engaged with said lower chamber for separation therefrom, said upper chamber having a top access opening and a lower opening, said upper chamber lower opening being adjacent said lower chamber upper opening for flow communication therebetween, whereby liquid introduced into said upper chamber through said top access opening flows from said upper chamber through said upper chamber lower opening and into said lower chamber through said lower chamber upper opening,
    c. closure means for said top access opening, and
    d. sealing means cooperative with said closure means for sealing each of said upper and lower openings upon closure of said top access opening by said closure means, said sealing means maintaining each of said lower opening of said upper chamber and said upper opening of said lower chamber sealed upon release of engagement between said upper and lower chambers and separation of said upper and lower chambers.

12. The receptacle of claim 11 wherein the lower sample chamber comprises:
    a. a base;
    b. a lower retaining well joined to the base;
    c. an access port formed in the well; and
    d. a flow guide within the access port.

13. The receptacle of claim 12 further comprising a plurality of access ports.

14. The receptacle of claim 13 further comprising a flow guide within each access port.

15. The receptacle of claim 12 further comprising a penetrable cap sleeve to selectively seal the access port and, when penetrated, release a fluid sample held within the lower sample chamber.

16. The receptacle of claim 12 further comprising a cap that removably conforms to the flow guide and, when the cap is removed, releases a fluid sample held within the lower sample chamber.

17. The receptacle of claim 11 wherein said closure comprises a vertical column having first and second ends with a lid for said top access opening joined to said first end, and wherein said sealing means comprises an upper plug at said second end and a lower plug releasably connected to said upper plug.

18. The receptacle of claim 17 wherein said lower opening of said upper chamber includes an annular groove and said upper plug includes a peripheral annular rib for sealingly mating reception in said upper chamber annular groove.

19. The receptacle of claim 18 wherein said upper opening of said lower chamber includes an annular groove and said lower plug includes a peripheral annular rib for sealingly mating reception in said lower chamber annular groove.

20. The receptacle of claim 18 in which said lower plug includes a recess having an annular groove and said upper plug includes a terminal portion receivable in said recess, said terminal portion having an annular rib for sealingly mating reception in said annular groove of said recess.

21. The receptacle of claim 17 wherein said upper plug is connected to said second end by a flexure and is sealingly engageable with said lower opening of said upper chamber, and wherein said lower plug is releasably connected to said upper plug and is sealingly engageable with said upper opening of said lower chamber.

22. The receptacle of claim 17 in which said lid includes at least one closed openable access aperture accessible with said top access opening maintained closed with said lid.

23. The receptacle of claim 21 wherein the lid and upper plug are threadedly engaged with the upper sample chamber and the lower plug is threadedly engageable with the lower sample chamber.

24. The receptacle of claim 21 wherein the lower sample chamber further comprises a retaining element to cooperatively engage a mating element on the plug.

25. The receptacle of claim 24 wherein the mating element comprises a projecting rim and wherein the retaining element comprises a keeper.

26. The receptacle of claim 21 wherein the lower plug is connected to the upper plug by a breakpiece.

27. The receptacle of claim 17 wherein said upper plug is sealingly engageable with said lower opening of said upper chamber, and wherein said lower plug comprises a flexure plate releasably connected to said upper plug and matingly and sealingly engageable with said upper opening of said lower chamber.

28. The receptacle of claim 27 in which said upper opening of said lower chamber comprises a shoulder and in which said lower plug includes a circumferential detent for capture of said shoulder.

29. The receptacle of claim 11 wherein said closure comprises a vertical column having first and second ends and a lid for said top access opening joined to said first end, and wherein said sealing means comprises
   (a) an upper plug at said second end for placement in said lower opening of said upper chamber upon closure of said top access opening by said closure means, and
   (b) a separate lower plug movably anchored to said lower chamber and extending upwardly into said upper chamber above said upper opening of said lower chamber for cooperative plug location sealing such upper opening of said lower chamber upon closure of said top access opening by said closure means and the associated placement of said upper plug in said lower opening of said upper chamber.

30. The receptacle of claim 11 in which the lower chamber includes a floor and at least one openable access aperture in such floor.

31. The receptacle of claim 30 in which said extendible and contractible portion comprises a bellows portion.

32. The receptacle of claim 31 in which said floor includes a plurality of upstanding vanes radially diverging from adjacent floor center to an annular upright coaxially bounded by said bellows portion.

33. The receptacle of claim 32 in which at least one closed access opening nozzle is vertically disposed between said floor center and said annular upright.

34. The receptacle of claim 11 in which the lower chamber includes an extendible and contractible portion to vary the volume of the lower chamber.

35. The receptacle of claim 11 in which said upper sample chamber includes at least one closed openable access aperture accessible with said top access opening maintained closed with said closure means.

36. A fluid sample receptacle comprising:
   a. an upper sample chamber having an upper access opening;
   b. a lower sample chamber releasably engaged with the upper sample chamber; said lower sample chamber comprising
      i. a base,
      ii. a variable volume bellows assembly joined to the base, and
      iii. an access aperture in a lower portion of the bellows assembly,
   c. a flow passage connecting said upper and lower chambers to conduct fluid from the upper sample chamber to the lower sample chamber; and
   d. a receptacle closure and seal, engageable with the upper sample chamber to close said upper access opening and seal the upper and lower sample chambers adjacent the flow passage.

37. The receptacle of claim 36 wherein the base and the bellows assembly are joined by friction heat welding.

38. The receptacle of claim 36 further comprising a key on the periphery of the base.

39. The receptacle of claim 36 wherein the base is covered with a tamper-evident seal.

40. A method of taking a fluid sample comprising the steps of:
   a. assembling an upper sample chamber to a lower sample chamber with a flow port between the chambers;
   b. placing a fluid sample in the upper sample chamber and allowing at least a portion of the fluid sample to flow through the flow port into the lower sample chamber;
   c. placing a receptacle top on the upper sample chamber to seal the fluid sample within the upper and lower sample chambers; and
   d. disengaging a plug from the receptacle top to permit disassembling the upper chamber from the lower chamber while retaining the fluid sample sealed within the upper and lower chambers.

41. A method of capturing a fluid sample, comprising:
   a. providing a fluid receptacle comprising (i) a lower chamber having an upper opening, (ii) an upper chamber releasably engaged with said lower chamber for separation therefrom, said upper chamber having a top access opening and a lower opening, said upper chamber lower opening being adjacent said lower chamber upper opening for flow communication therebetween, (iii) closure means for said top access opening, and (iv) sealing means cooperative with said closure means for sealing each of said upper and lower openings upon closure of said top access opening by said closure means;
   b. entering a liquid sample through said top access opening of said upper chamber, whereby liquid introduced into said upper chamber through said top access opening flows from said upper chamber through said upper chamber lower opening and into said lower chamber through said lower chamber upper opening;
   c. applying said closure means to close said top access opening and cooperatively with the closure means applying said sealing means to seal each of said lower opening of said upper chamber and said upper opening of said lower chamber
   d. separating said upper and lower chambers with said sealing means respectively maintaining sealing of said lower opening of said upper chamber and said upper opening of said lower chamber upon release of engagement between said upper and lower chambers.

* * * * *